US011817216B2

(12) United States Patent
Yamada et al.

(10) Patent No.: US 11,817,216 B2
(45) Date of Patent: Nov. 14, 2023

(54) SEARCH METHOD AND INFORMATION PROCESSING SYSTEM

(71) Applicant: Genomedia Inc., Tokyo (JP)

(72) Inventors: Tomoyuki Yamada, Tokyo (JP); Masato Nishihara, Tokyo (JP)

(73) Assignee: GENOMEDIA INC., Tokyo (JP)

( * ) Notice: Subject to any disclaimer, the term of this patent is extended or adjusted under 35 U.S.C. 154(b) by 80 days.

(21) Appl. No.: 17/601,547

(22) PCT Filed: Apr. 9, 2019

(86) PCT No.: PCT/JP2019/015532
§ 371 (c)(1),
(2) Date: Nov. 10, 2021

(87) PCT Pub. No.: WO2020/208729
PCT Pub. Date: Oct. 15, 2020

(65) Prior Publication Data
US 2022/0199256 A1 Jun. 23, 2022

(51) Int. Cl.
*G16H 50/20* (2018.01)
*G06N 20/00* (2019.01)
(Continued)

(52) U.S. Cl.
CPC ......... *G16H 50/20* (2018.01); *G06F 18/2113* (2023.01); *G06N 20/00* (2019.01); *G06T 7/0012* (2013.01); *G06T 2207/20081* (2013.01)

(58) Field of Classification Search
CPC .... G16H 50/20; G06F 18/2113; G06N 20/00; G06N 20/20; G06T 7/0012; G06T 2207/20081
(Continued)

(56) References Cited

U.S. PATENT DOCUMENTS

2011/0131158 A1\* 6/2011 Furukawa .............. G06N 20/10
706/12
2019/0087532 A1\* 3/2019 Madabhushi ........ G06V 10/454
2019/0316203 A1\* 10/2019 Davison .............. C12Q 1/6886

FOREIGN PATENT DOCUMENTS

JP 2005-182696 A 7/2005
JP 2006-099565 A 4/2006
(Continued)

OTHER PUBLICATIONS

Diba Ali et al., "DeepCAMP:Deep Convolutional Action & Attribute Mid-Level Patterns", 2016 IEEE Conference on Computer Vision and Pattern Recognition (CVPR), IEEE, Jun. 27, 2016 (Jun. 27, 2016), pp. 3557-3565, XP033021540, DOI:10.1109/CVPR.2016. 387 (Year: 2016).\*

(Continued)

*Primary Examiner* — Joy Chng
(74) *Attorney, Agent, or Firm* — PEARNE & GORDON LLP

(57) ABSTRACT

A search method of searching for a feature that affects an output result of a machine learning model, the search method includes: a first step of applying, to all training data, at least one or more separate filters combining at least one or more feature presence/absence determining devices that determine presence or absence of a feature on a plurality of sets of correct answer data that is positive and correct answer data that is negative and information on whether the pieces of the data is positive; a second step of applying the pieces of training data generated in the first step to separate machine learning to separately execute machine learning; and a third step of outputting information that extracts a new feature using a verification result obtained by inputting verification data to separate machine learning after the machine learning.

9 Claims, 15 Drawing Sheets

(51) Int. Cl.
  *G06F 18/2113* (2023.01)
  *G06T 7/00* (2017.01)
(58) Field of Classification Search
  USPC .......................................................... 705/2–3
  See application file for complete search history.

(56) References Cited

FOREIGN PATENT DOCUMENTS

| | | |
|---|---|---|
| JP | 2011-113550 A | 6/2011 |
| JP | 2018-524990 A | 9/2018 |

OTHER PUBLICATIONS

Diba Ali et al., "Deep visual words: Improved fisher vector for image classification", 2017 Fifteenth IAPR International Conference on Machine Vision Application (MVA), MVA Organization, May 8, 2017 (May 8, 2017), pp. 186-189, XP033126605, DOI:10.23919/MVA.2017.7986832 (Year: 2017).*

Extended European search report issued in European Patent Application No. 19924390.8 dated Oct. 21, 2022.

Ali Diba et al., "DeepCAMP: Deep Convolutional Action & Attribute Mid-Level Patterns", 2016 IEEE Conference on Computer Vision and Pattern Recognition, Jun. 27, 2016, pp. 3557-3565.

Ali Diba et al., "Deep Visual Words: Improved Fisher Vector for Image Classification", 2017 Fifteenth IAPR International Conference on Machine Vision Applications, May 8, 2017, pp. 186-189, Nagoya, Japan.

Yanling Tian et al., "Selective Multi-Convolutional Region Feature Extraction based Iterative Discrimination CNN for Fine-Grained Vehicle Model Recognition", 2018 24th International Conference on Pattern Recognition, Aug. 20, 2018, pp. 3279-3284, Beijing, China.

Written Opinion and International Preliminary Report on Patentability ssued in Patent Application No. PCT/JP2019/015532 dated Jul. 16, 2019.

International Search Report issued in Patent Application No. PCT/JP2019/015532 dated Jul. 16, 2019.

Koizumi K. "What is machine learning and deep learning? Part 2", IoT News, Jan. 27, 2016, Japan, https://iotnews.jp/archives/11680—Concise Explanation in Spec. Para. [0002].

Japanese Office Action issued in Japanese Patent Application No. 2021-513080 dated Mar. 28, 2023.

* cited by examiner

FIG.2
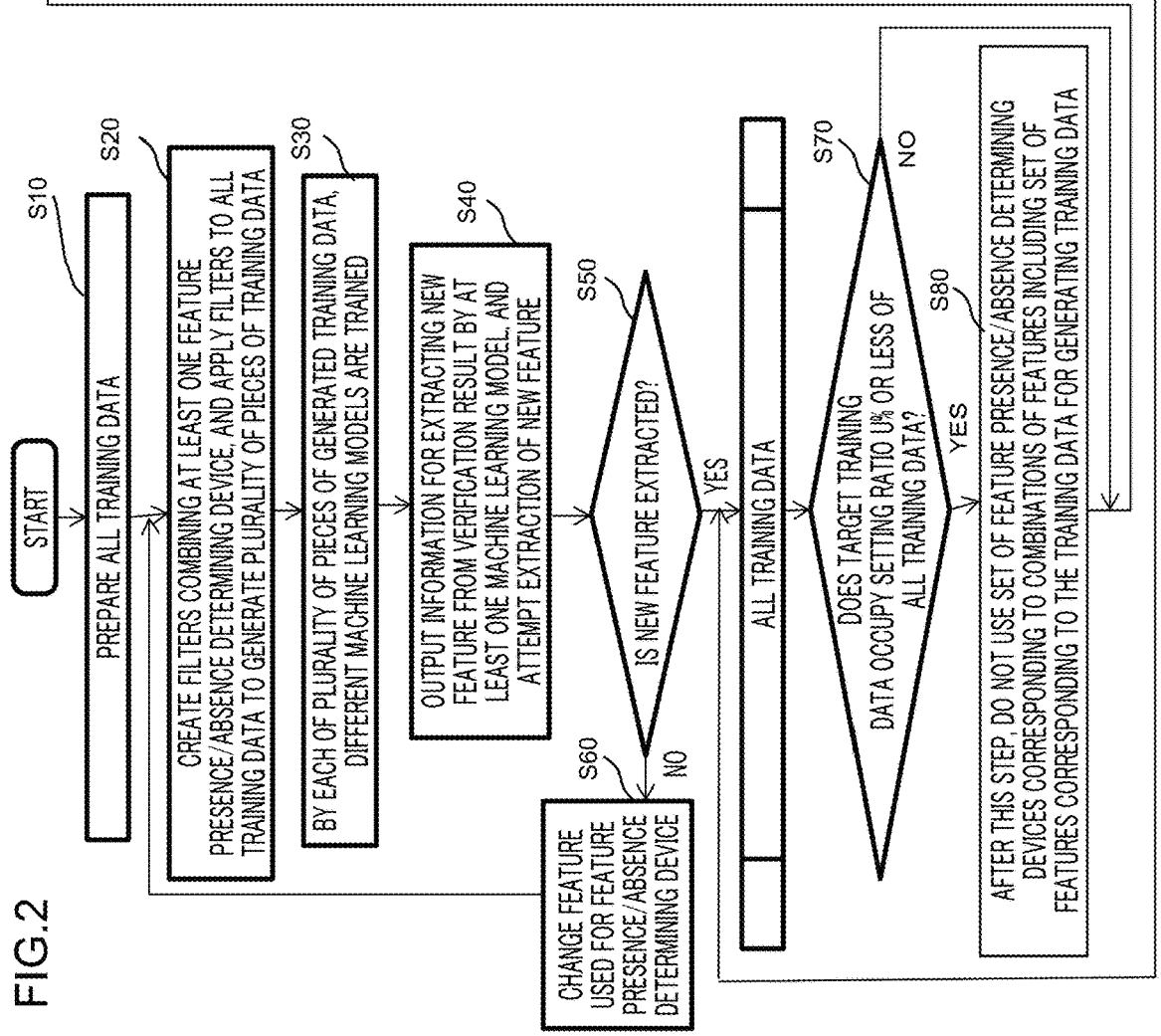
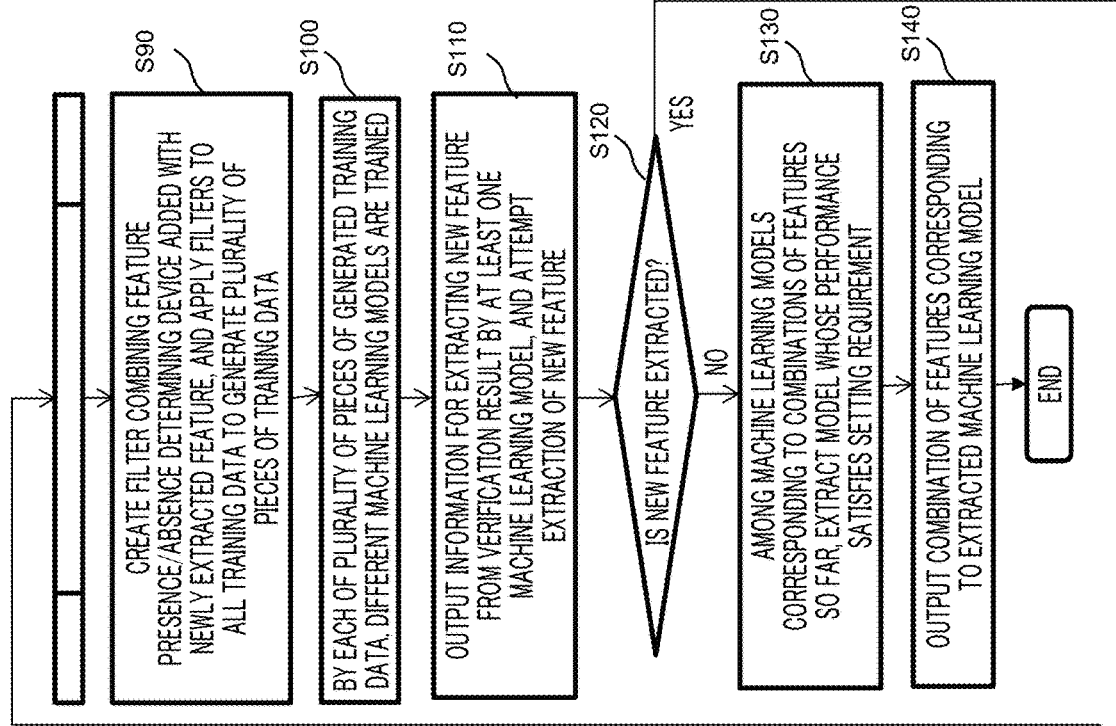

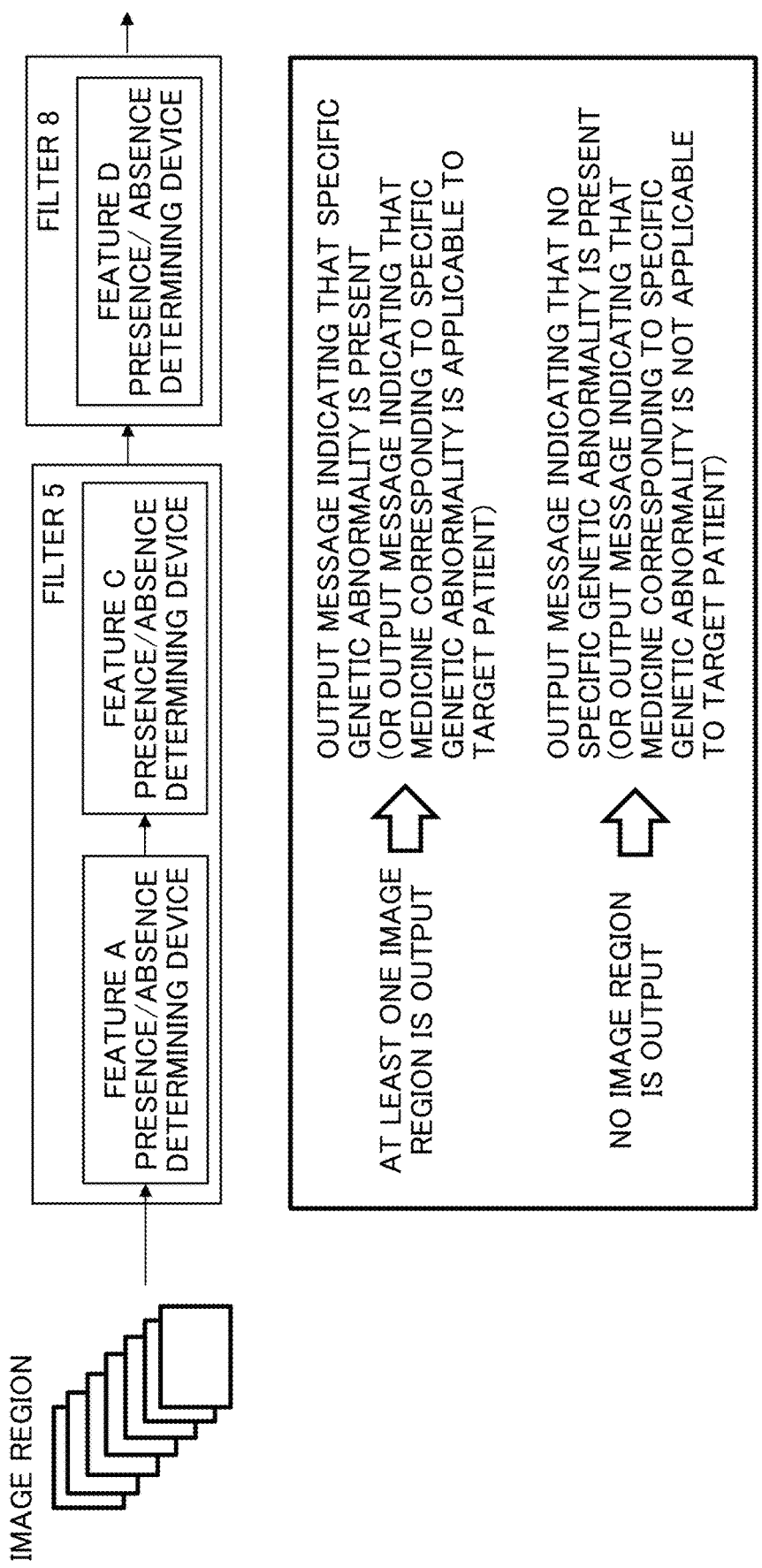

SEARCH METHOD AND INFORMATION PROCESSING SYSTEM

TECHNICAL FIELD

The present invention relates to a search method and an information processing system.

BACKGROUND ART

In machine learning (e.g. deep learning), it is possible to output correct answers to unknown data by learning from pairs of known data (e.g. in the case of images, images of dogs and cats) and correct answers to the data (e.g. information on whether the data is a dog or a cat) as teacher data. Training is conducted using a set of correct answers (e.g. information on whether it is a dog or cat), and thus a correct answer can be output to unknown data

CITATION LIST

Non Patent Literature

Non Patent Literature 1: https://iotnews.jp/archives/11680

SUMMARY OF INVENTION

Technical Problem

However, in conventional machine learning (e.g. deep learning), although correct answers can be output by training, there is a problem that it is unclear what features in the known data are used to output the correct answers. That is, there is a problem that a feature that affects the output result of the machine learning model is unknown.

An aspect of the present invention has been made in view of the above problems, and an object is to provide a search method and an information processing system capable of interpreting a feature that affects an output result of a machine learning model.

Solution to Problem

A search method of searching for a feature that affects an output result of a machine learning model, the search method according to a first aspect of the present invention comprises: a first step of applying, to all training data, at least one or more separate filters combining at least one or more feature presence/absence determining devices that determine presence or absence of a feature on a plurality of sets of correct answer data that is positive and correct answer data that is negative and information on whether the pieces of the data is positive; a second step of applying the pieces of training data generated in the first step to separate machine learning to separately execute machine learning; and a third step of outputting information that extracts a new feature using a verification result obtained by inputting verification data to separate machine learning after the machine learning.

According to this configuration, it is possible to obtain a new feature that affects the output result of the machine learning model from the information that extracts new features.

The search method according to a second aspect of the present invention, in the search method according to the first aspect, further comprising: a fourth step of determining whether the training data occupies a setting ratio or less of all the training data on the pieces of training data generated in the first step; a fifth step of excluding, as a result of the determination in the fourth step, when the training data occupies a setting ratio or less of all the training data, a set of feature presence/absence determining devices corresponding to a combination of features including a set of features corresponding to the training data; a sixth step of applying, to at least one or more pieces of all the training data, separate filters configured of at least one or more sets except the excluded set of feature presence/absence determining devices in the at least one feature presence/absence determining device and a feature presence/absence determining device that determines whether the presence or absence of the newly extracted feature; a seventh step of applying the pieces of training data generated in the sixth step to separate machine learning to separately execute machine learning; and an eighth step of outputting, after the machine learning in the seventh step, information that extracts a new feature using a verification result obtained by inputting verification data to the separate machine learning.

According to this configuration, search efficiency can be improved by searching for a new feature while narrowing a search range.

The search method according to a third aspect of the present invention, in the search method according to the second aspect, further comprising a ninth step in which when a new feature is extracted in the eighth step, the fourth step is further executed on the pieces of training data generated in the sixth step, the fifth step, the sixth step, the seventh step, and the eighth step are repeated correspondingly, and when no new feature is extracted after the information that extracts a new feature is output in the eighth step, a machine learning model having performance that satisfies a setting requirement is extracted from machine learning models corresponding to combinations of features so far, and a combination of features corresponding to the extracted machine learning model is output.

According to this configuration, the combination of features output in the ninth step is a combination of features that affect the output result of the machine learning model, and thus it is possible to acquire a combination of features that affect the output result of the machine learning model.

The search method according to a fourth aspect of the present invention, in the search method according to any one of the first to the third aspect, the search method is a search method of searching for a feature that is a feature of an image of a target object and that affects an output result of whether a specific abnormality is present in the target object, in the first step, at least one or more separate filters combining at least one or more feature presence/absence determining devices that determine presence or absence of a feature are applied, to all training data, on a plurality of sets of an image of a target object having a specific abnormality and an image of a target object having no specific abnormality and information whether the target objects from which the images are obtained have a specific abnormality, and the feature that affects the output result of the machine learning model is a feature that determines whether a specific abnormality is present in the target object.

According to this configuration, it is possible to search for a feature that affects the output result of whether a specific abnormality is present in the target object.

The search method according to a fifth aspect of the present invention, in the search method according to the fourth aspect, wherein the target object is cancerous tissue of a patient, the image of the target object is a pathological image of cancerous tissue of the patient, the specific abnormality is a specific genetic abnormality, and in the first step, at least one or more separate filters combining at least one or more feature presence/absence determining devices that determine presence or absence of a feature are applied, to all training data, on a plurality of sets of an image region of a pathological image of cancerous tissue with a specific genetic abnormality and an image region of a pathological image of cancerous tissue with no specific genetic abnormality or normal tissue and information on whether a specific genetic abnormality is present in a patient's tissue from which each image region has been obtained.

According to this configuration, it is possible to obtain a combination of features of a pathological image of cancerous tissue with a specific genetic abnormality, the features affecting the output result of the presence or absence of the specific genetic abnormality of the cancer tissue.

An information processing system to a sixth aspect of the present invention, comprises an output unit configured to output information on whether the specific abnormality is present in a target object or information on whether a medicine corresponding to the specific abnormality is applicable to the target object by filtering a target image with a filter of a combination of features determined by the search method described in the third aspect.

According to this configuration, information on whether the specific abnormality is present in the target object or information on whether the medicine corresponding to the specific abnormality is applicable to the target object is output from the image of the target object, and thus it is possible to provide an index on whether the medicine corresponding to the specific abnormality can be prescribed to the target patient in a shorter period of time.

The information processing system to a seventh aspect of the present invention, in the information processing system according to the sixth aspect, wherein the filter is a filter using a trained machine learning model machine-learned using training data filtered by a filter of a combination of features determined by the search method described in the third aspect for all training data.

According to this configuration, the trained machine learning model is used, and thus it is possible to improve the prediction accuracy on whether the specific abnormality is present in the target object or whether the medicine corresponding to the specific abnormality is applicable to the target object.

The information processing system to an eighth aspect of the present invention, in the information processing system according to the sixth or seventh aspect, wherein the target object is cancerous tissue of a target patient, the image of the target object is a pathological image of cancerous tissue of a target patient, the specific abnormality is a specific genetic abnormality, and the output unit outputs information on whether the specific genetic abnormality is present in the cancerous tissue of the target patient or information on whether a medicine corresponding to the specific genetic abnormality is applicable to the target patient by filtering each of image regions obtained by dividing a pathological image of the cancerous tissue of the target patient using a filter with a combination of features determined by the search method described in the third aspect.

According to this configuration, information on whether the specific genetic abnormality is present in the cancerous tissue of the target patient or information on whether the medicine corresponding to the specific genetic abnormality is applicable to the target patient is output from the pathological image, and thus it is possible to provide an index on whether the medicine corresponding to the specific genetic abnormality can be prescribed to the target patient in a shorter period of time than DNA sequencing.

Advantageous Effects of Invention

According to an aspect of the present invention, it is possible to obtain a new feature that affects the output result of the machine learning model from the information that extracts new features.

BRIEF DESCRIPTION OF DRAWINGS

FIG. 2 is a flowchart illustrating an example of a flow of a search method according to the present embodiment.

FIG. 15 is a schematic diagram that describes processing of an output unit according to a modification of the present embodiment.

DESCRIPTION OF EMBODIMENTS

In the following, an embodiment and an example of the embodiment will be described with reference to the drawings. However, unnecessarily detailed description may be omitted. For example, a detailed description of a well-known matter and a redundant description of substantially the same configuration may be omitted. This is to avoid unnecessary redundancy of the following description and to facilitate understanding of those skilled in the art.

Embodiment

In addition to the above problem, the present embodiment is to solve a problem in which it is not possible to solve a problem having an unknown feature that affects an output result of a machine learning (e.g. deep learning) model, while making the affecting feature interpretable. In addition, in a machine learning (e.g. deep learning) model, there is also a problem that target performance is not obtained when teacher data is randomly prepared.

In order to solve these problems, the present embodiment is to provide a search method of searching for a feature (or a combination of features) that affects an output result of a machine learning model. As a result, only the training data filtered by the combination of the features for all training data is used, and thus it is possible to improve the performance of the machine learning model. As a result, it is possible to solve a problem by the machine learning model while making a feature that affects learning of the machine learning model interpretable.

In the present embodiment, as an example of a search method of searching for a feature that affects the output result of the machine learning model, a search method of searching for a feature that affects the output result of the presence or absence of a specific abnormality (e.g. genetic abnormalities) of a target object, which is a feature of an image of the target object, will be described.

Figure 1:
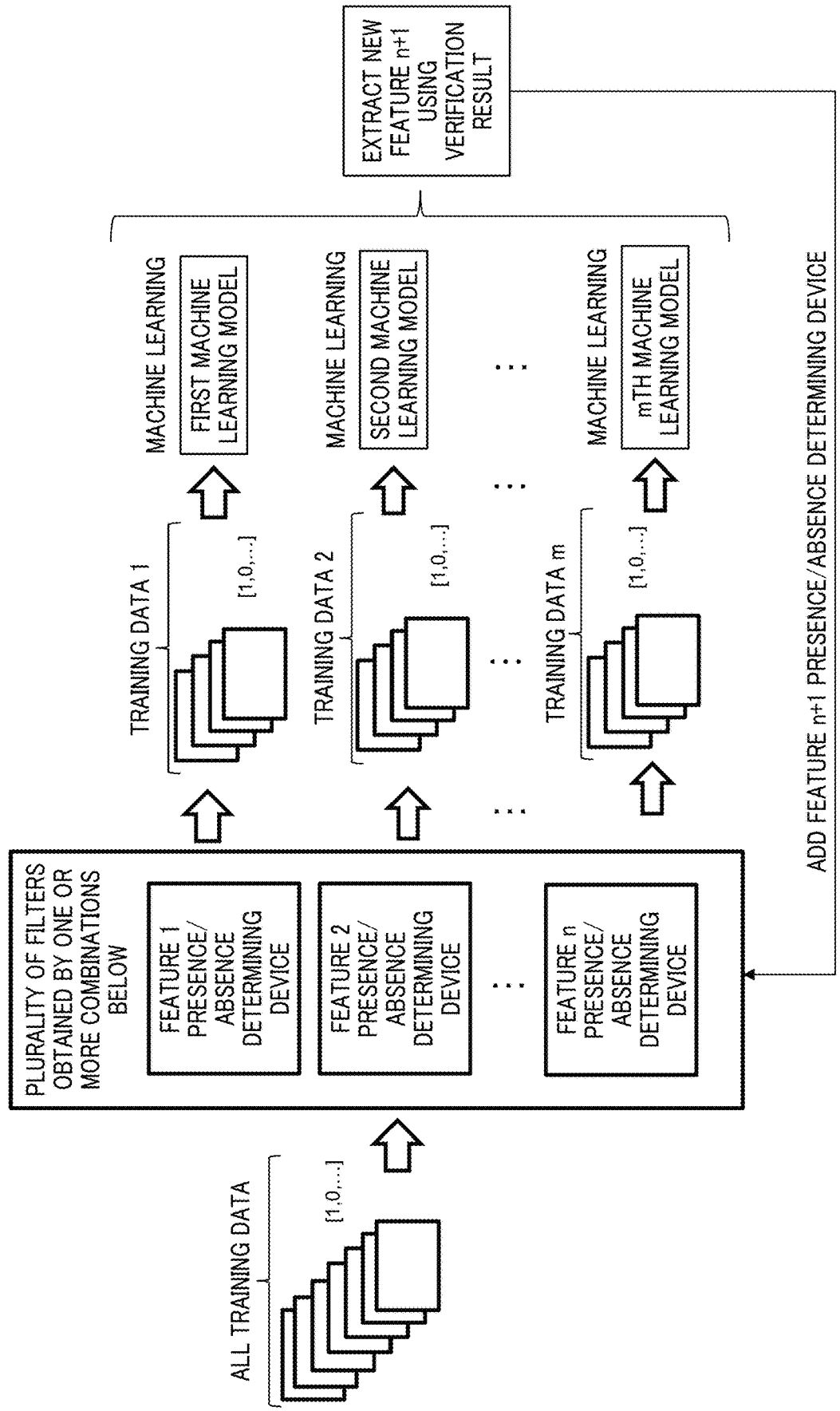
FIG. 1 is a schematic diagram that describes a search method of the present embodiment.

FIG. 1 is a schematic diagram that describes a search method according to the present embodiment. As illustrated in FIG. 1, an image of a target object (image data) and information (information of 0 or 1) on whether a specific abnormality is present in a target object are prepared as all training data. It is assumed that there are 1 to n (n is a natural number) candidate features for a specific abnormality. A feature 1 presence/absence determining device that determines the presence or absence of feature 1, a feature 2 presence/absence determining device that determines the presence or absence of feature 2, . . . , and a feature n presence/absence determining device that determines the presence or absence of feature n are prepared. Then, m filters obtained by combining at least one or more of the feature 1 presence/absence determining device, the feature 2 presence/absence determining device, . . . , and the feature n presence/absence determining device are prepared.

For example, the case will be described in which the feature 1 presence/absence determining device determines that feature 1 is present (e.g. the tumor cell ratio is 50% or more), and for example, the feature 2 presence/absence determining device determines that feature 2 is present (e.g. there is viscosity). In this case, for example, in the case in which a filter, filter i, (i is a natural number from 1 to m) among the m filters is a filter combining the feature 1 presence/absence determining device and the feature 2 presence/absence determining device, when this filter of all training data is applied, for example, only data in which feature 1 is present in the image and feature 2 is not present in all training data is output as training data i.

By applying m filters to all training data, m pieces of training data from training data 1 to training data m are output.

Using the training data 1, a first machine learning model executes machine learning (e.g. training of deep learning) and using training data 2, a second machine learning model executes machine learning (e.g. training of deep learning). Similarly, an ith machine learning model executes machine learning (e.g. training of deep learning) using training data i, and an mth machine learning model executes machine learning (e.g. training of deep learning) using training data m.

After training, by inputting data, which has not been used for training of a part of training data 1, to the first machine learning model to the mth machine learning model as verification data, information up to 0 to 1 is output, and these pieces of information up to 0 to 1 are compared with a threshold value (e.g. 0.8). In the case in which the comparison result is equal to or greater than the threshold value (e.g. 0.8), information indicating a positive (e.g. 1) is output, and in the case in which the comparison result is less than the threshold value (e.g. 0.8), information indicating a negative (e.g. 0) is output.

The output result can be divided into four types: True Positive (TP), False Positive (FP), False Negative (FN), and True Negative (TN).

Here, True Positive (TP) is a prediction correctly predicting that the correct answer data, which is positive, is positive.

False Positive (FP) is a prediction erroneously predicting that correct answer data, which is negative, is positive.

False negative (FN) is a prediction erroneously predicting that correct answer data, which is positive, is negative.

True Negative (TN) is a prediction correctly predicting that correct answer data, which is negative, is negative.

For example, when the output result is equal to or greater than a threshold value (e.g. 0.9), correct answer data is positive, and when the output result is less than the threshold value (e.g. 0.8), correct answer data is negative.

Using these verification results, information that extracts a new feature n+1 is output. This information may be an image whose output result is positive (or negative), or may be at least one or more of a TP image, a TN image, an FP image, and a TN image.

Then, a new feature n+1 is extracted using this information. At this time, a new feature n+1 may be extracted using the verification results in descending order of the performance evaluation values (e.g. area under an ROC curve (AUC)) of the machine learning. Here, the ROC curve is a curve connecting points based on the false positive rate and the true positive rate when the threshold is changed.

Furthermore, at the time of extracting a new feature n+1, for example, an image with a positive (or negative) output result may be checked with the eyes of a person (e.g. a doctor such as a pathologist) to search for any common feature.

Alternatively, at the time of extracting the new feature n+1, for example, at least one or more of a TP image, a TN image, an FP image, and a TN image may be checked with the eyes of a person (e.g. a doctor such as a pathologist) to search for the new feature n+1.

Alternatively, a new feature n+1 may be extracted by executing another software or program.

In the case in which a new feature n+1 is extracted, a feature n+1 presence/absence determining device that determines the presence or absence of the new feature n+1 is added. Subsequently, p (p is a natural number) filters are prepared in which at least one or more of the feature 1 presence/absence determining device, the feature 2 presence/absence determining device, . . . , the feature n presence/absence determining device, and the feature n+1 presence/absence determining device is combined.

By applying the p filters to all training data, p pieces of training data from training data 1 to training data p are output.

Similarly, the first machine learning model executes machine learning (e.g. training of deep learning) using training data 1, and the second machine learning model executes machine learning (e.g. training of deep learning) using the training data 2. Similarly, the ith machine learning model executes machine learning (e.g. training of deep learning) using training data i, and the pth machine learning model executes machine learning (e.g. training of deep learning) using training data p.

After training, by inputting data, which has not been used for training of a part of training data 1, to the first machine learning model to the pth machine learning model as verification data, information up to 0 to 1 is output, and these pieces of information up to 0 to 1 are compared with a threshold value (e.g. 0.8). In the case in which the comparison result is equal to or greater than the threshold value (e.g. 0.8), information indicating a positive (e.g. 1) is output, and in the case in which the comparison result is less than the threshold value (e.g. 0.8), information indicating a negative (e.g. 0) is output.

Using these verification results, information that extracts a new feature n+2 is output. Using this information, the new feature n+2 is extracted.

Next, a search method of searching for a feature that affects the output result of the machine learning model according to the present embodiment will be described with reference to FIG. 2.

FIG. 2 is a flowchart illustrating an example of a flow of a search method according to the present embodiment.

(Step S10) First, all training data is prepared.

(Step S20) Subsequently, a filter combining at least one feature presence/absence determining device is created, and a plurality of pieces of training data is generated by applying each filter to all training data.

(Step S30) Subsequently, by each of the plurality of pieces of generated training data, different machine learning models are trained.

(Step S40) Subsequently, information for extracting a new feature is output from the verification result by the at least one machine learning model, and extraction of a new feature is attempted.

(Step S50) Subsequently, it is determined whether a new feature is extracted.

(Step S60) In the case in which no new feature is extracted in Step S50, the feature used in the feature presence/absence determining device is changed.

In the case in which a new feature is extracted in Step S50, Step S70 is executed for all the pieces of training data.

(Step S70) It is determined whether the target training data occupies the setting ratio U % or less of all the pieces of training data.

(Step S80) In the case in which the target training data occupies the setting ratio U % or less of all the pieces of training data in Step S70, in the following step, a set of feature presence/absence determining devices corresponding to combinations of features (e.g. all combinations including feature A and feature B, such as a combination of feature A and feature B and a combination of feature A, feature B, and feature C) including a set of features (e.g. feature A and feature B) corresponding to the training data is not used for generating training data.

Figure 7:
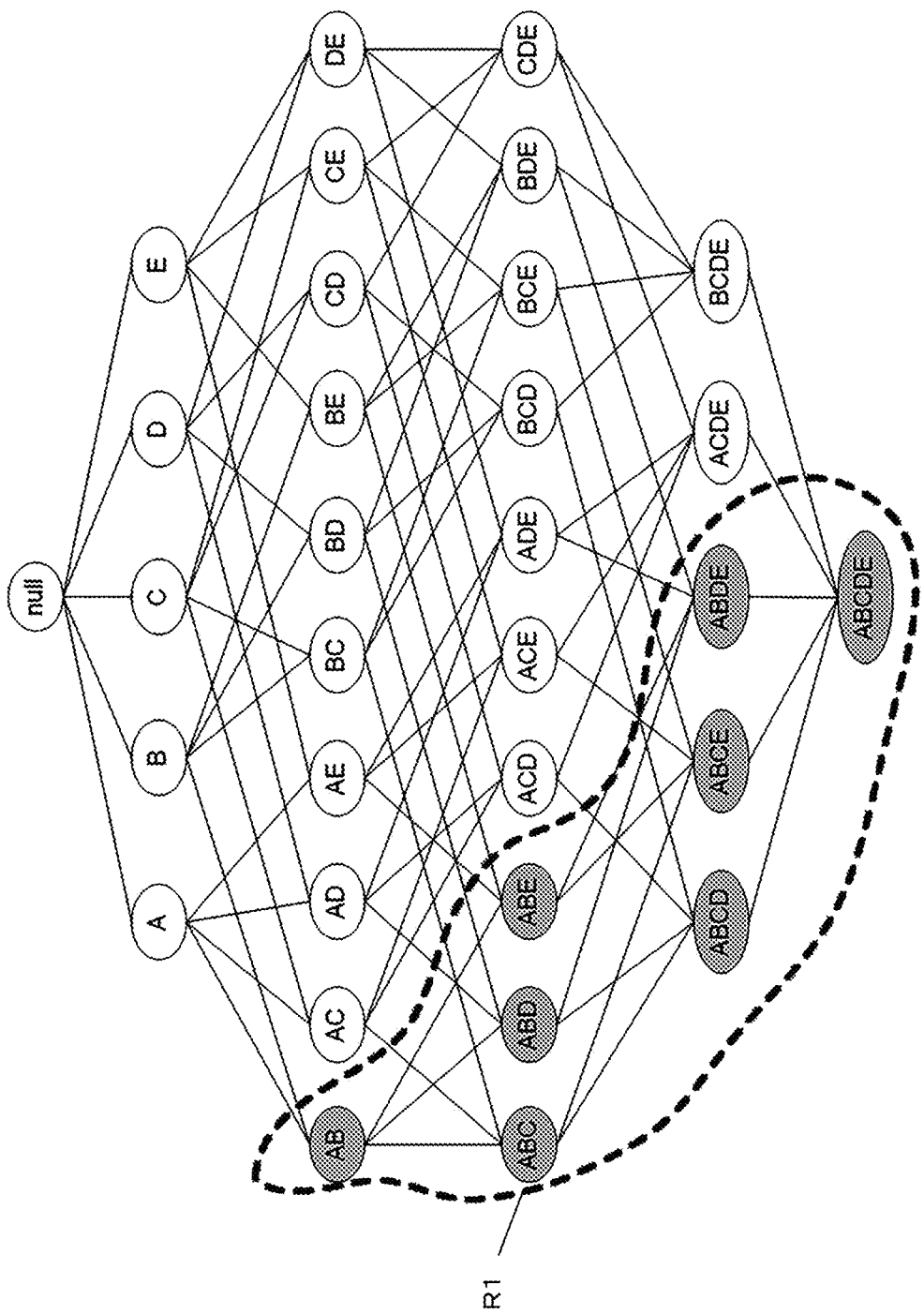
FIG. 7 is a fourth schematic diagram that describes a search method according to an example.

For example, as illustrated in FIG. 7, in the case in which the training data that is positive in the feature A presence/absence determining device and is positive in the feature B presence/absence determining device occupies a setting ratio U % or less of all training data, the training data that is positive in the feature A presence/absence determining device and is positive in the feature B presence/absence determining device and is positive in the feature X presence/absence determining device also occupies a setting ratio U % or less of all training data. Therefore, it is assumed that the data having the specific abnormality is a half of all training data, when the data of the setting ratio U % is statistically significantly less than the data of the half of all training data (e.g. less than 5% of a half of all training data), it can be statistically determined that there is a high possibility that the data having feature A and feature B is not the common matter of the data having the specific abnormality. As a result, the search range can be narrowed, and the search can be efficiently performed.

(Step S90) Filters combining feature presence/absence determining devices to which a newly extracted feature is added are created and the filters are applied to all training data to generate a plurality of pieces of training data.

(Step S100) Subsequently, by each of the plurality of pieces of generated training data, different machine learning models are trained.

(Step S110) Subsequently, information for extracting a new feature is output from the verification result by the at least one machine learning model, and extraction of a new feature is attempted.

(Step S120) Subsequently, it is determined whether a new feature is extracted. In the case in which a new feature is extracted, the process returns to Step S70, and the steps after Step S70 are repeated.

(Step S130) In the case in which no new feature is extracted in Step S120, among machine learning models corresponding to combinations of features so far, a machine learning model whose performance satisfies the setting requirement (e.g. those having an AUC of 0.9 or more) is extracted.

(Step S140) A combination of features corresponding to the machine learning model extracted in Step S130 is output. As a result, it is possible to obtain a combination of features that affect the output result of the machine learning model.

As described above, the search method according to the present embodiment is a search method of searching for a feature that affects an output result of a machine learning model, the search method including: a first step of applying, to all training data, at least one or more separate filters combining at least one or more feature presence/absence determining devices that determine the presence or absence of a feature on a plurality of sets of correct answer data that is positive and correct answer data that is negative and information on whether the pieces of the data is positive (corresponding to step S20); a second step of applying the pieces of training data generated in the first step to separate machine learning to separately execute machine learning (corresponding to step S30); and a third step of outputting information that extracts a new feature using a verification result obtained by inputting verification data to separate machine learning after the machine learning (corresponding to Step S40).

According to this configuration, it is possible to obtain a new feature that affects the output result of the machine learning model from the information that extracts new features.

Furthermore, the search method according to the present embodiment includes: a fourth step of determining whether the training data occupies a setting ratio or less of all the training data on the pieces of training data generated in the first step (corresponding to Step S70); a fifth step of excluding, as a result of the determination in the fourth step, when the training data occupies a setting ratio or less of all the training data, a set of feature presence/absence determining devices corresponding to a combination of features including a set of features corresponding to the training data (corresponding to Step S80); a sixth step of applying, to at least one or more pieces of all the training data, separate filters configured of at least one or more sets except the excluded set of feature presence/absence determining devices in the at least one feature presence/absence determining device and a feature presence/absence determining device that determines whether the presence or absence of the newly extracted feature (corresponding to Step S90); a seventh step of applying the pieces of training data generated in the sixth step to separate machine learning to separately execute machine learning (corresponding to Step S100); and an eighth step of outputting, after the machine learning in the seventh step, information that extracts a new feature using a verification result obtained by inputting verification data to the separate machine learning (corresponding to Step S110).

With this configuration, a new feature is searched while narrowing the search range, and thus it is possible to improve search efficiency.

Furthermore, the search method according to the present embodiment further has a ninth step in which when a new feature is extracted in the eighth step, the fourth step is further executed, in the sixth step, on the pieces of training data generated, the fifth step, the sixth step, the seventh step, and the eighth step are repeated correspondingly, and when no new feature is extracted in the eighth step after the information that extracts a new feature is output in the eighth step, a machine learning model having performance that satisfies a setting requirement is extracted from machine learning models corresponding to combinations of features so far, and a combination of features corresponding to the extracted machine learning model is output (corresponding to Steps S130 and S140).

According to this configuration, the combination of features output in the ninth step is a combination of features that affect the output result of the machine learning model, and thus it is possible to acquire a combination of features that affect the output result of the machine learning model.

Furthermore, the search method described as an example in the present embodiment is a search method of searching for a feature that is a feature of an image of a target object and that affects an output result of whether a specific abnormality is present in the target object. In the first step, at least one or more separate filters combining at least one or more feature presence/absence determining devices that determine the presence or absence of a feature are applied, to all training data, on a plurality of sets of an image of a target object with a specific abnormality and an image of a target object with no specific abnormality and information whether the target objects from which the images are obtained have a specific abnormality. The feature that affects the output result of the machine learning model is a feature that determines whether a specific abnormality is present in the target object.

With this configuration, it is possible to search for a feature that affects the output result of whether a specific abnormality is present in the target object.

EXAMPLES

In the present example, the target object is cancerous tissue of a patient, the image of the target object is a pathological image of the cancerous tissue of the patient, and the specific abnormality is a specific genetic abnormality. That is, in the present example, as an example of a search method of searching for a feature that is a feature of an image of a target object and that affects the output result of the presence or absence of a specific abnormality of the target object, a search method of searching for a feature that is a feature of a pathological image of cancerous tissue with a specific genetic abnormality and that affects the output result of the presence or absence of the specific genetic abnormality of the cancerous tissue will be described.

Background of the Present Example

The trigger of cancer is a genetic abnormality, and the cancer is developed when the gene is damaged, cells proliferate extensively, and the elimination by the immune system fails to catch up. Therefore, when the genetic abnormality causing abnormal proliferation is found and the corresponding medicine is given, cancer can be effectively suppressed. In order to realize this, preparation of an oncogene panel test in which a specimen is collected from cancerous tissue or the like extracted from a patient and analyzed is in progress in Japan. Here, the "panel" refers to a set in which a plurality of genes is combined.

Problems of Present Example

In the oncogene panel test, a DNA sequence of a cancer cell is read by a DNA sequencer, and whether a specific genetic abnormality has not occurred in the read DNA sequence is analyzed. As a result of this analysis, when a specific genetic abnormality has occurred, a doctor will prescribe a medicine corresponding to the specific genetic abnormality. The reading of the DNA sequence by the DNA sequencer takes at least one week, and the entire period of the oncogene panel test is generally said to be four to six weeks. For a target patient who has developed a specific cancer or progressive cancer, there is a risk that the symptoms of the cancer further progress by waiting for this period, and thus it is desirable to determine whether a medicine corresponding to a specific genetic abnormality can be prescribed to the target patient in a shorter period of time.

The present example has been made in view of the above problems, and in addition to the above problems, an object is to provide a search method and an information processing system capable of providing an index on whether a medicine corresponding to a specific genetic abnormality can be prescribed to a target patient in a shorter period of time.

Figure 3:
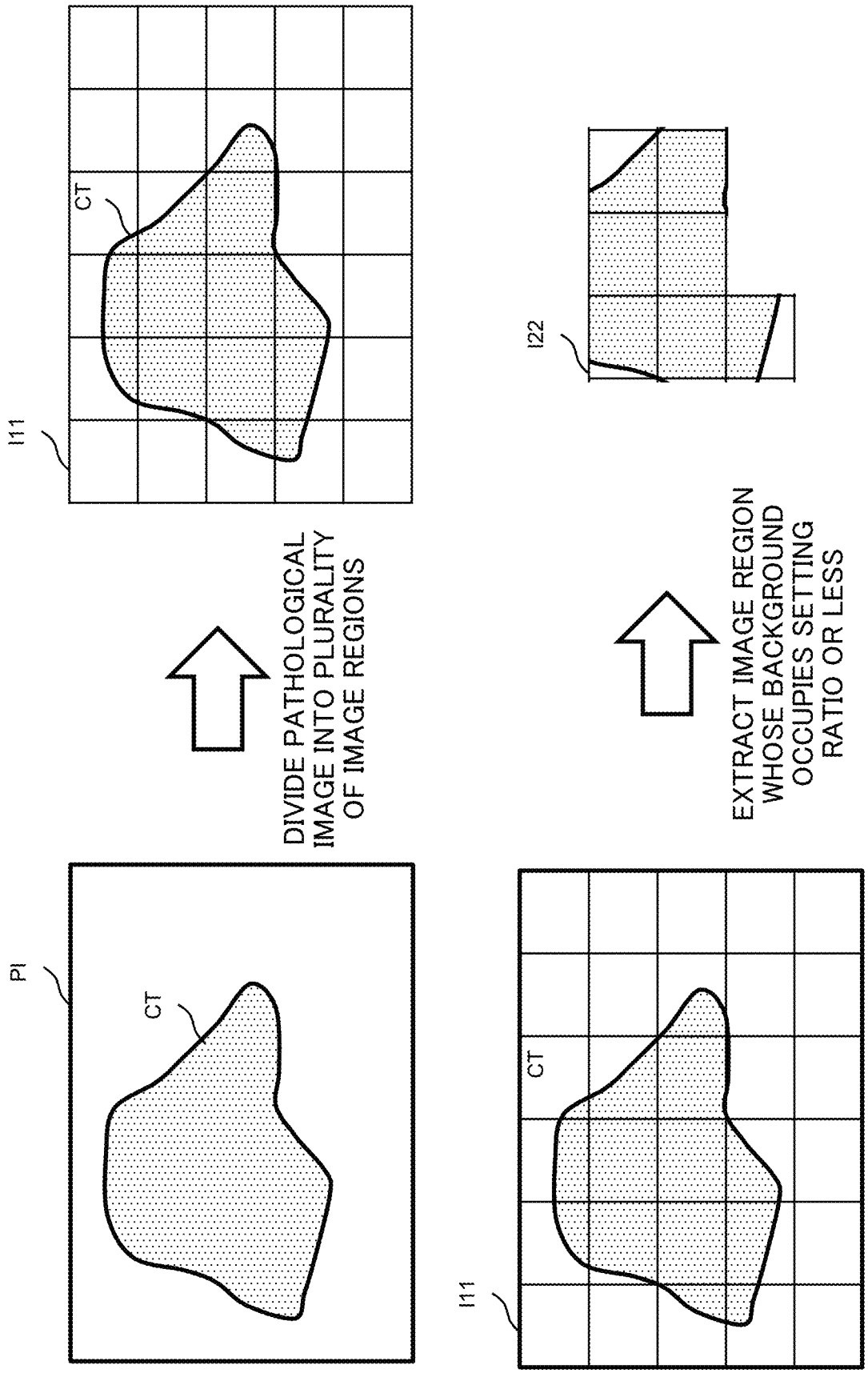
FIG. 3 is a diagram that describes a method of extracting an image region of a pathological image used in the present example.

FIG. 3 is a diagram that describes a method of extracting an image region of a pathological image used in the present example. As illustrated in FIG. 3, a pathological image PI of cancerous tissue CT is divided into a plurality of image regions (e.g. an image region I11). Next, an image area in which the background occupies a set ratio or less is extracted. As a result, for example, an image region I22 is extracted.

Figure 4:
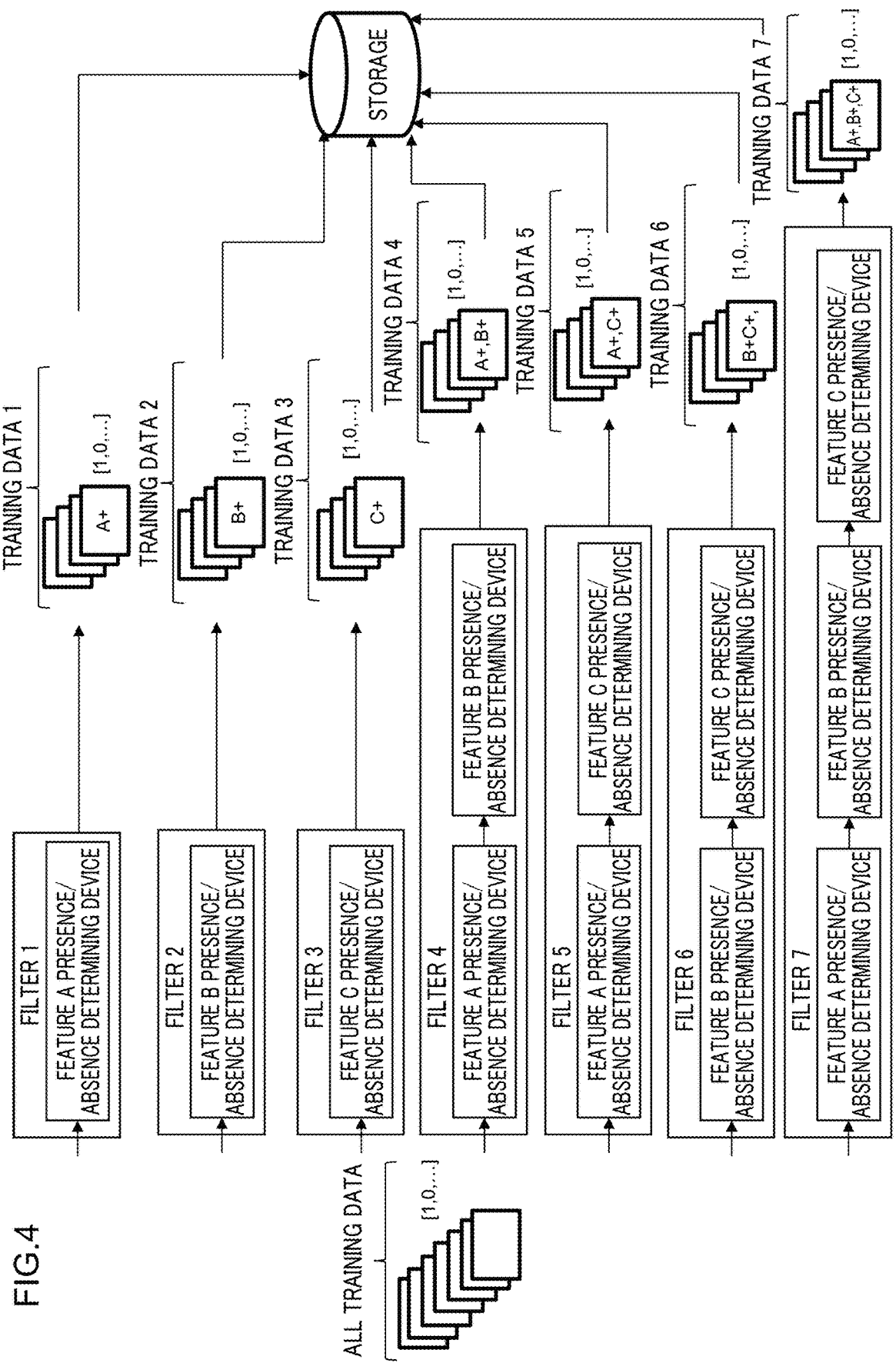
FIG. 4 is a first schematic diagram that describes a search method according to an example.

FIG. 4 is a first schematic diagram that describes a search method of the present example. Here, description will be made in which feature A, feature B, and feature C are assumed as candidate features. The all training data illustrated in FIG. 4 includes, as an example, a plurality of sets of a past image region of a pathological image of cancerous tissue with a specific genetic abnormality and a past image region of a pathological image of cancerous tissue with no specific genetic abnormality or normal tissue and information on whether a specific genetic abnormality is present in a patient's tissue from which each image region is obtained. Here, as an example, it is assumed that all training data is stored in a storage.

As illustrated in FIG. 4, a filter 1 that passes data having feature A by a feature A presence/absence determining device that determines the presence/absence of the feature A, a filter 2 that passes data having feature B by a feature B presence/absence determining device that determines the presence/absence of feature B, and a filter 3 that passes an image having feature C by a feature C presence/absence determining device that determines the presence/absence of feature C are prepared.

In addition, as illustrated in FIG. 4, a filter 4 that passes an image having feature A and having feature B by the feature A presence/absence determining device and the feature B presence/absence determining device, a filter 5 that passes an image having feature A and having feature C by the feature A presence/absence determining device and the feature C presence/absence determining device, and a filter 6 that passes an image having feature B and having feature C by the feature B presence/absence determining device and the feature C presence/absence determining device are prepared.

In addition, as illustrated in FIG. 4, a filter 7 that passes an image having feature A, feature B, and feature C by the feature A presence/absence determining device, the feature B presence/absence determining device, and the feature C presence/absence determining device is prepared.

All the image regions included in all training data are passed through the filters 1 to 7. The training data 1 is a set of each image region that has passed through the filter 1 and information on whether a specific genetic abnormality is present in the tissue of the patient from which the image region has been obtained, and the image region included in training data 1 is an image region having feature A. Similarly, training data 2 is a set of each image region that has passed through the filter 2 and information on whether a specific genetic abnormality is present in the tissue of the patient from which the image region has been obtained, and the image region included in the training data 2 is an image region having feature B. Similarly, training data 3 is a set of each image region that has passed through the filter 3 and information on whether a specific genetic abnormality is present in the tissue of the patient from which the image region has been obtained, and the image region included in the training data 3 is an image region having the feature C.

Similarly, training data 4 is a set of each image region that has passed through the filter 4 and information on whether a specific genetic abnormality is present in the tissue of the patient from which the image region has been obtained, and the image region included in the training data 4 is an image region having feature A and feature B.

Similarly, training data 5 is a set of each image region that has passed through the filter 5 and information on whether a specific genetic abnormality is present in the tissue of the patient from which the image region has been obtained, and the image region included in the training data 5 is an image region having feature A and feature C.

Similarly, training data 6 is a set of each image region that has passed through the filter 6 and information on whether a specific genetic abnormality is present in the tissue of the patient from which the image region has been obtained, and the image region included in the training data 6 is an image region having feature B and feature C.

Similarly, training data 7 is a set of each image region that has passed through the filter 7 and information on whether a specific genetic abnormality is present in the tissue of the patient from which the image region has been obtained, and the image region included in the training data 7 is an image region having feature A, feature B, and feature C. The training data 1 to the training data 7 are stored in a storage.

Figure 5:
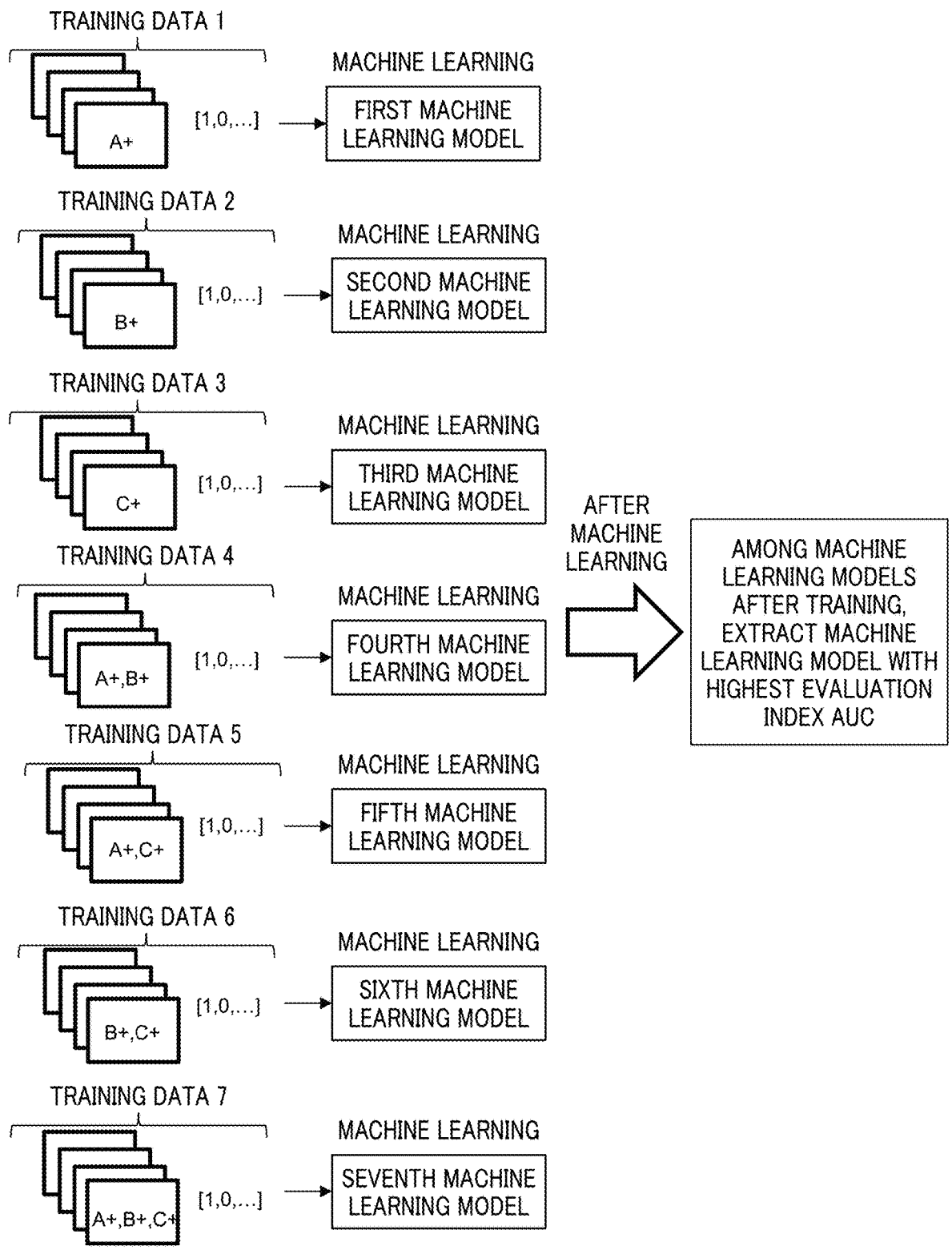
FIG. 5 is a second schematic diagram that describes a search method according to an example.

FIG. 5 is a second schematic diagram that describes a search method according to the example. As illustrated in FIG. 5, the first machine learning model to the seventh machine learning model execute machine learning using corresponding training data 1 to training data 7, respectively. After the machine learning, as an example, a machine learning model with the highest evaluation index AUC is extracted from the machine learning models after training.

Figure 6:
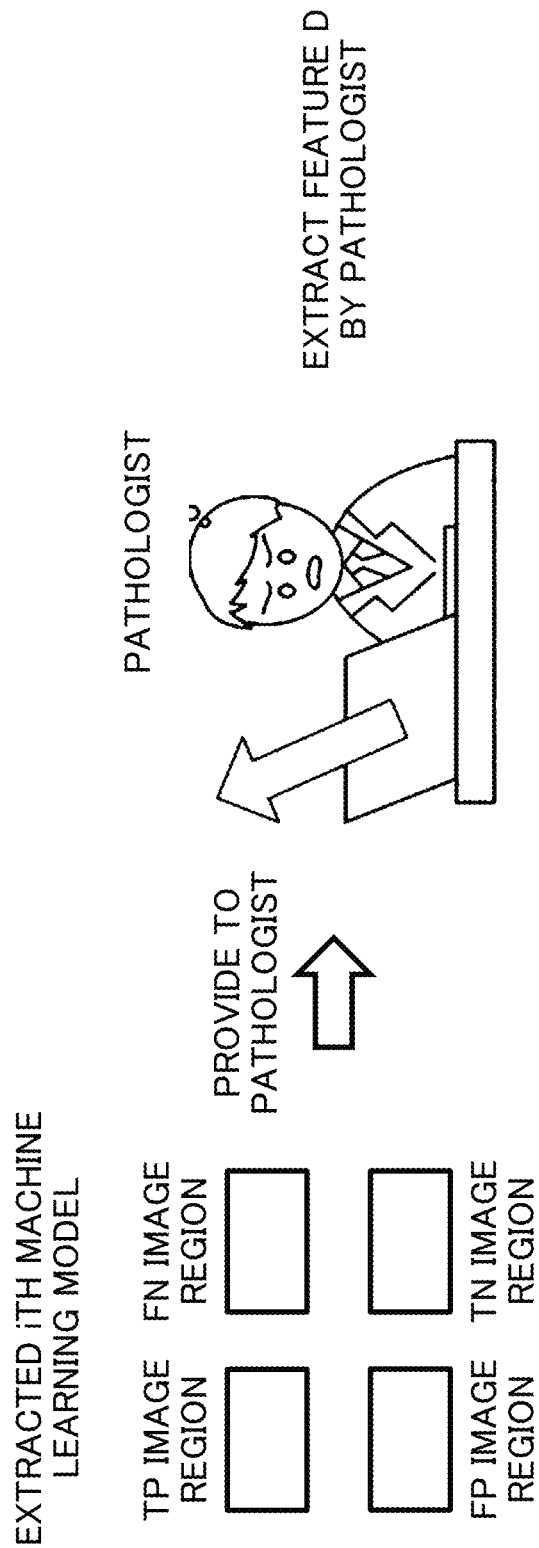
FIG. 6 is a third schematic diagram that describes a search method according to an example.

FIG. 6 is a third schematic diagram that describes a search method according to the example. Here, as an example, in FIG. 5, it is assumed that the extracted machine learning model is an ith machine learning model.

Using the output result (here, prediction information on whether a specific genetic abnormality is present in the patient's tissue from which the image region of the verification data has been obtained) output by inputting the verification data to the ith machine learning model, the TP image region, the FN image region, the FP image region, and the TN image region are generated, for example. The TP image region, the FN image region, the FP image region, and the TN image region are provided to, for example, a pathologist. The pathologist compares the TP image region, the FN image region, the FP image region, and the TN image region, and extracts feature D (e.g. with thick mucus) characteristic in the image of the cancerous tissue with a specific genetic abnormality.

FIG. 7 is a fourth schematic diagram that describes a search method according to the example. In the fourth machine learning model, in all training data, training data 4 that is positive in the feature A presence/absence determining device and positive in the feature B presence/absence determining device is used for training.

Example of Method of Excluding Search Range of Combination of Features

In the case in which the training data that is positive in the feature A presence/absence determining device and is positive in the feature B presence/absence determining device occupies a setting ratio U % or less of all training data, the training data that is positive in the feature A presence/absence determining device and is positive in the feature B presence/absence determining device and is positive in the feature X presence/absence determining device (X is an unknown feature) also occupies a setting ratio U % or less of all training data. Therefore, it is assumed that the data having the specific abnormality is a half of all training data, when the data of the setting ratio U % is statistically significantly less than the data of the half of all training data (e.g. less than 5% of a half of all training data), it can be statistically determined that there is a high possibility that the data having feature A and feature B is not the common matter of the data having the specific abnormality. Therefore, the combination in the broken line region R1 in FIG. 7 can be excluded from the search range. In the following step, a set of feature presence/absence determining devices corresponding to combinations of features including feature A and feature B (e.g. all combinations including feature A and feature B, such as a combination of feature A and feature B and a combination of feature A, feature B, and feature C) is not used for generating training data. As a result, the search range can be narrowed, and the search can be efficiently performed.

Figure 8:
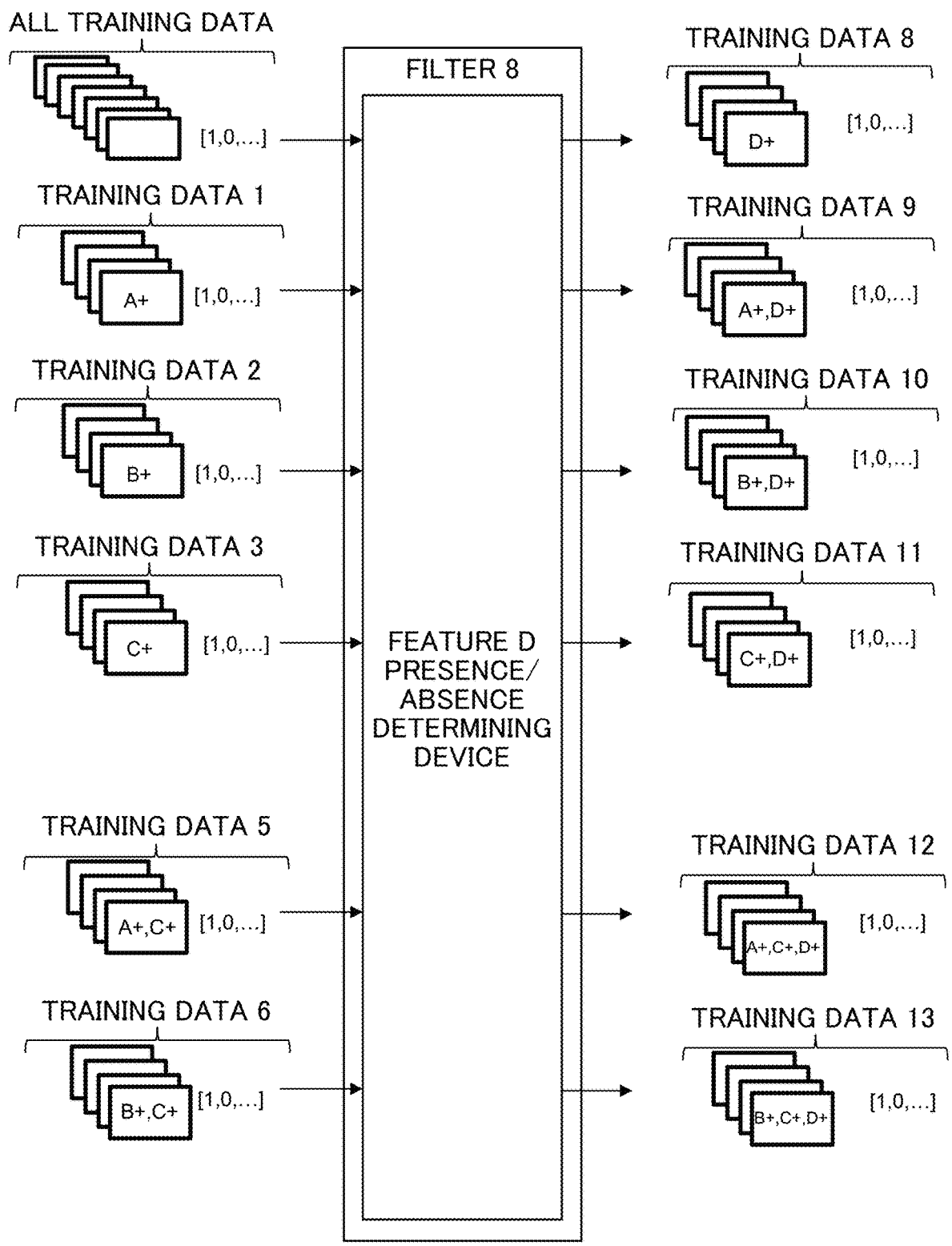
FIG. 8 is a fifth schematic diagram that describes a search method according to an example.

FIG. 8 is a fifth schematic diagram that describes a search method according to the example. Here, as an example, processes will be described in which a process after feature D is extracted as a new feature in FIG. 6 and it is determined that a set of feature presence/absence determining devices corresponding to a combination of features including feature A and feature B is not used for generating training data as illustrated in FIG. 7.

A filter 8 that passes data having feature D is prepared by a feature D presence/absence determining device that determines the presence or absence of feature D.

Subsequently, all the image regions included in all training data stored in the storage are passed through the filter 8. Training data 8 is a set of each image region that has passed through the filter 8 and information on whether a specific genetic abnormality is present in the tissue of the patient from which the image region has been obtained, and the image region included in the training data 8 is an image region having feature D.

In addition, all the image regions included in the training data 1 stored in the storage are passed through the filter 8. Training data 9 is a set of each image region that has passed through the filter 8 and information on whether a specific genetic abnormality is present in the tissue of the patient from which the image region has been obtained, and the image region included in the training data 9 is an image region having feature A and feature D.

In addition, all the image regions included in the training data 2 stored in the storage are passed through the filter 8. Training data 10 is a set of each image region that has passed through the filter 8 and information on whether a specific genetic abnormality is present in the tissue of the patient from which the image region has been obtained, and the image region included in the training data 10 is an image region having a feature B and a feature D.

In addition, all the image regions included in the training data 3 stored in the storage are passed through the filter 8. Training data 11 is a set of each image region that has passed through the filter 8 and information on whether a specific genetic abnormality is present in the tissue of the patient from which the image region has been obtained, and the image region included in the training data 11 is an image region having feature C and feature D.

In addition, all the image regions included in the training data 5 stored in the storage are passed through the filter 8. Training data 12 is a set of each image region that has passed through the filter 8 and information on whether a specific genetic abnormality is present in the tissue of the patient from which the image region has been obtained, and the image region included in training data 12 is an image region having feature A, feature C, and feature D.

In addition, all the image regions included in the training data 6 stored in the storage are passed through the filter 8. Training data 13 is a set of each image region that has passed through the filter 8 and information on whether a specific genetic abnormality is present in the tissue of the patient from which the image region has been obtained, and the image region included in training data 13 is an image region having feature B, feature C, and feature D.

Figure 9:
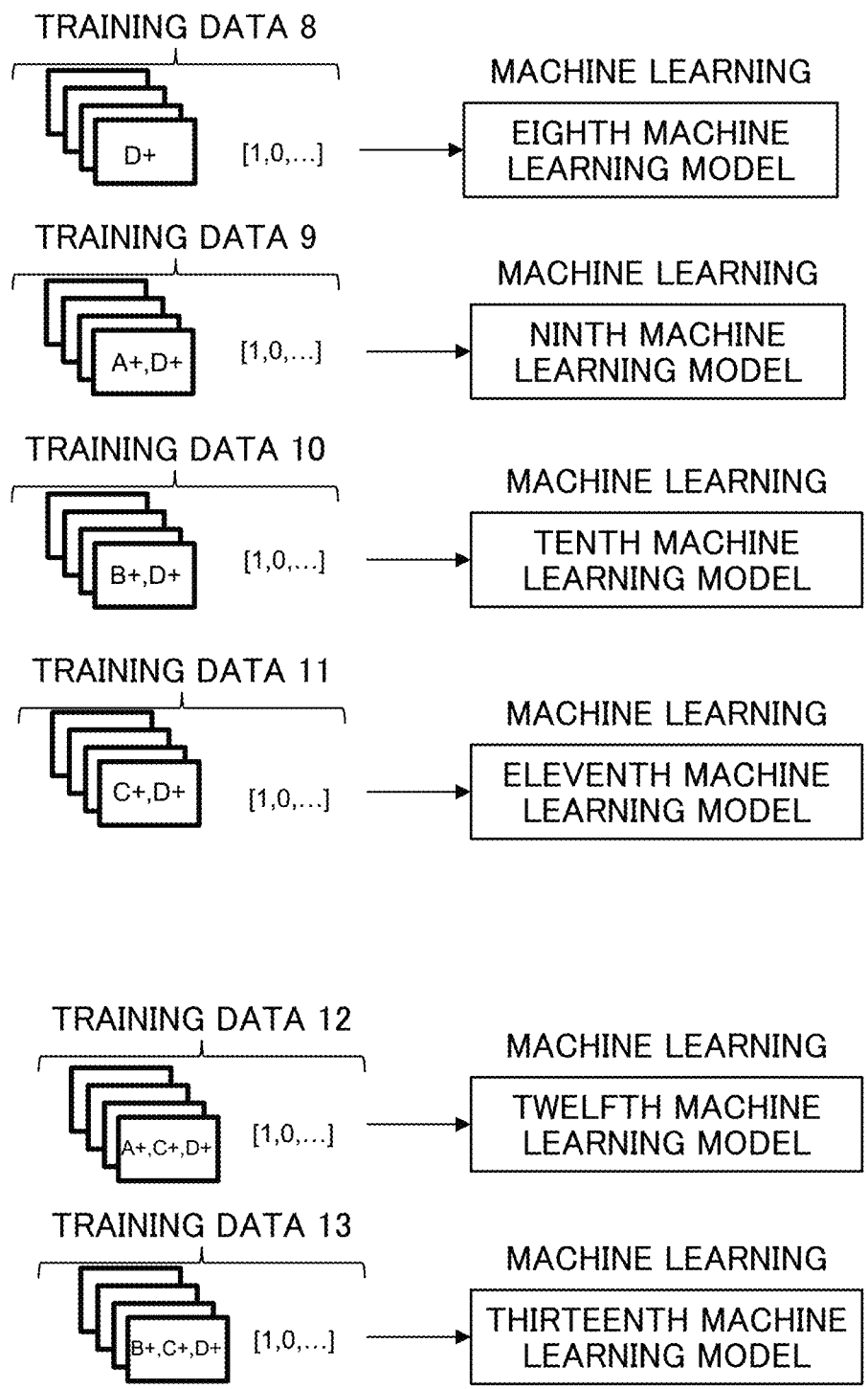
FIG. 9 is a sixth schematic diagram that describes a search method according to an example.

FIG. 9 is a sixth schematic diagram that describes a search method according to the example. As illustrated in FIG. 9, the eighth machine learning model to the thirteenth machine learning model execute machine learning using the corresponding training data 8 to training data 13, respectively.

Figure 10:
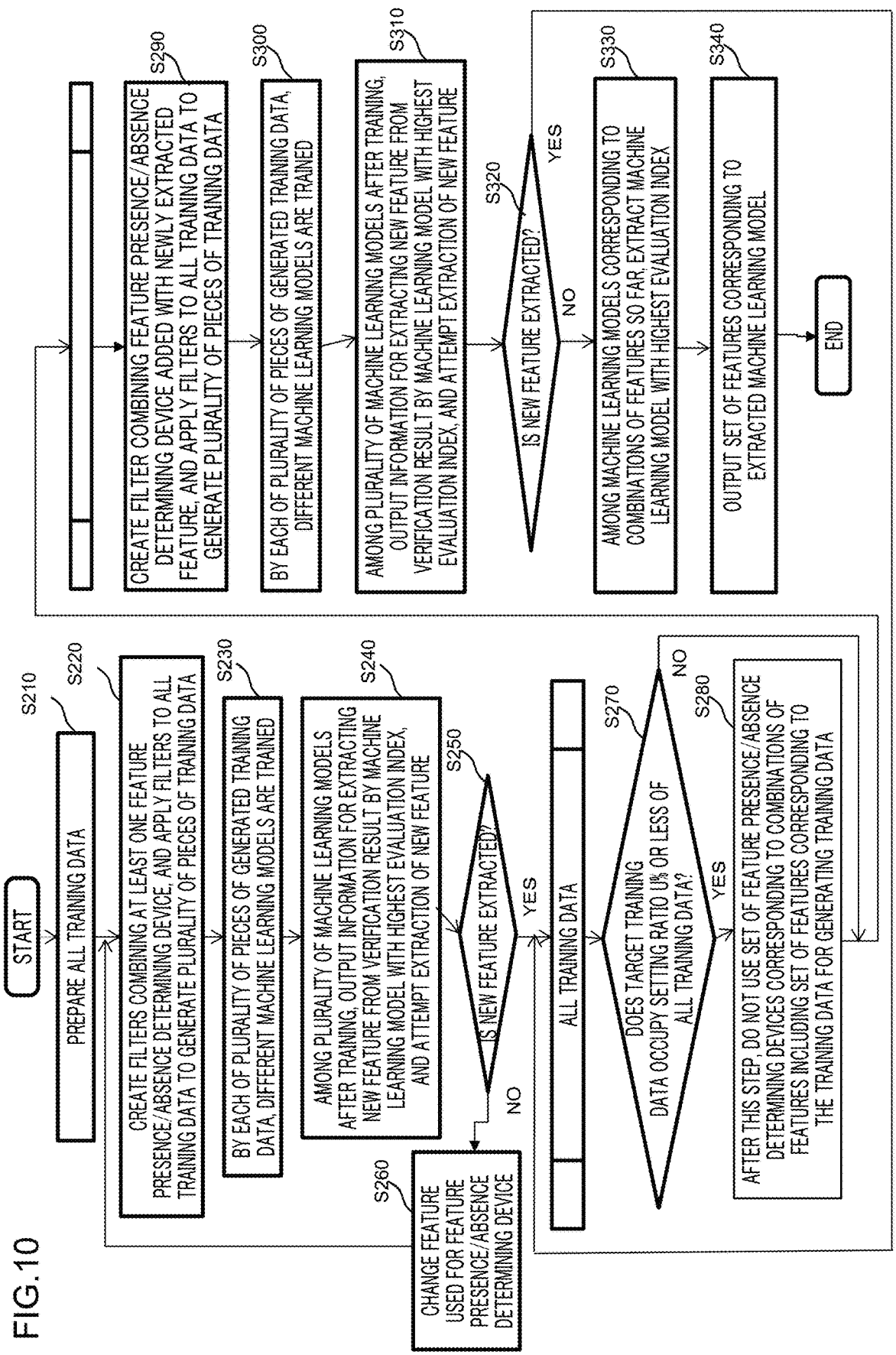
FIG. 10 is a flowchart illustrating an example of a flow of a search method according to the present example.

Next, a search method of searching for a feature of a pathological image of cancerous tissue of a patient, the feature affecting the output result of the presence or absence of a specific abnormality in the cancerous tissue of the patient according to the present example will be described with reference to FIG. 10. FIG. 10 is a flowchart illustrating an example of a flow of a search method according to the present example.

(Step S210) First, all training data is prepared.

(Step S220) Subsequently, a filter combining at least one feature presence/absence determining device is created, and a plurality of pieces of training data is generated by applying each filter to all training data.

(Step S230) Subsequently, by each of the plurality of pieces of generated training data, different machine learning models are trained.

(Step S240) Subsequently, information for extracting a new feature is output from the verification result of the machine learning model with the highest evaluation index (e.g. AUC) among the plurality of machine learning models after training, and extraction of a new feature is attempted.

(Step S250) Subsequently, it is determined whether a new feature is extracted.

(Step S260) In the case in which no new feature is extracted in Step S250, the feature used in the feature presence/absence determining device is changed.

In the case in which a new feature is extracted in Step S250, Step S270 is executed for all the pieces of training data.

(Step S270) It is determined whether the target training data occupies the setting ratio U % or less of all the pieces of training data.

(Step S280) In the case in which the target training data occupies the setting ratio U % or less of all the pieces of training data in Step S270, in the following step, a set of feature presence/absence determining devices corresponding to the combination of features (e.g. all combinations including feature A and feature B, such as a combination of feature A and feature B and a combination of feature A, feature B, and feature C) including the set of features (e.g. feature A and feature B) corresponding to the training data is not used for generating the training data.

For example, as illustrated in FIG. 7, in the case in which the training data that is positive in the feature A presence/absence determining device and is positive in the feature B presence/absence determining device occupies a setting ratio U % or less of all training data, the training data that is positive in the feature A presence/absence determining device and is positive in the feature B presence/absence determining device and is positive in the feature X presence/absence determining device also occupies a setting ratio U % or less of all training data. Therefore, it is assumed that the data having the specific abnormality is a half of all training data, when the data of the setting ratio U % is statistically significantly less than the data of the half of all training data (e.g. less than 5% of a half of all training data), it can be statistically determined that there is a high possibility that the data having feature A and feature B is not the common matter of the data having the specific abnormality. As a result, the search range can be narrowed, and the search can be efficiently performed.

(Step S290) Filters combining feature presence/absence determining devices to which a newly extracted feature is added are created and the filters are applied to all training data to generate a plurality of pieces of training data.

(Step S300) Subsequently, by each of the plurality of pieces of generated training data, different machine learning models are trained.

(Step S310) Subsequently, information for extracting a new feature is output from the verification result of the machine learning model with the highest evaluation index among the plurality of machine learning models after training, and extraction of a new feature is attempted.

(Step S320) Subsequently, it is determined whether a new feature is extracted. In the case in which a new feature is extracted, the process returns to Step S270, and the steps after Step S270 are repeated.

(Step S330) In the case in which no new feature is extracted in Step S320, a machine learning model with the highest evaluation index (e.g. AUC) is extracted from machine learning models corresponding to combinations of features so far.

(Step S340) A combination of features corresponding to the machine learning model extracted in Step S130 is output. As a result, it is possible to obtain a combination of features that is a feature of a pathological image of cancerous tissue with a specific genetic abnormality and that affects the output result of the presence or absence of the specific genetic abnormality of the cancerous tissue.

As described above, in the search method according to the present embodiment, in the first step, at least one or more separate filters combining at least one or more feature presence/absence determining devices that determine the presence or absence of a feature are applied, to all training data, on a plurality of sets of an image region of a pathological image of cancerous tissue with a specific genetic abnormality and an image region of a pathological image of cancerous tissue with no specific genetic abnormality or normal tissue and information on whether a specific genetic abnormality is present in a patient's tissue from which each image region has been obtained.

According to this configuration, it is possible to obtain a combination of features of a pathological image of cancerous tissue with a specific genetic abnormality, the features affecting the output result of the presence or absence of the specific genetic abnormality of the cancer tissue.

Figure 11:
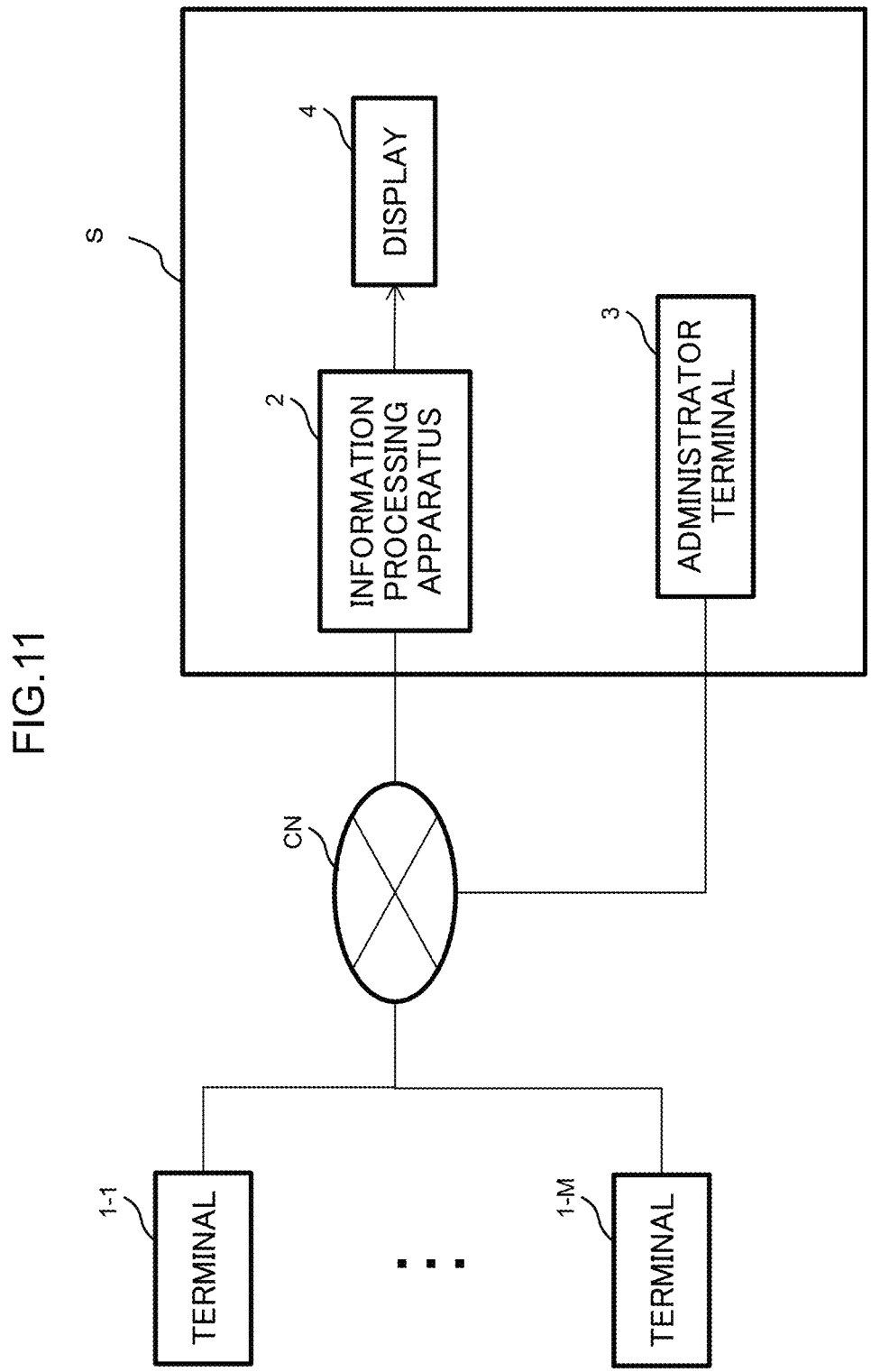
FIG. 11 is a schematic configuration diagram of an information processing system according to the present embodiment.

FIG. 11 is a schematic configuration diagram of an information processing system according to the present embodiment. As illustrated in FIG. 11, an information processing system S includes an information processing apparatus 2 connected to terminals 1-1 to 1-M (M is a natural number) via a communication circuit network CN, an administrator terminal 3 connected to the information processing apparatus 2 via the communication circuit network CN, and a display 4 connected to the information processing apparatus 2.

The terminals 1-1 to 1-M are terminal devices used by a hospital person such as a clinician, a pathologist, or an assistant of a doctor (e.g. a nurse), and transmit a target image (here, as an example, a pathological image of cancerous tissue of a target patient) to the information processing apparatus 2 in response to an operation by the hospital person. For example, in the case in which the information processing apparatus 2 is installed in a medical institution and receives an image of a target (here, as an example, a pathological image of cancerous tissue of the target patient) transmitted from the terminals 1-1 to 1-M, the information processing apparatus 2 outputs information corresponding to the image of the target (here, as an example, a pathological image of cancerous tissue of the target patient) and transmits the information to the terminals 1-1 to 1-M.

This information is information on whether a specific abnormality is present in the target object (e.g. cancerous tissue of a target patient). In the present embodiment, as an example, this information is information on whether a specific abnormality is present in the cancerous tissue of the target patient, or information on whether a medicine corresponding to the specific genetic abnormality is applicable to the target patient.

The display 4 may display the above information according to a video signal output from the information processing apparatus 2.

The administrator terminal 3 is a terminal device used by a management organization that manages the information processing system S according to the present embodiment. The information processing system S may or may not include the terminals 1-1, ..., and 1-M. However, in the present embodiment, the information processing system S will be described as not including the terminals 1-1, ..., and 1-M.

Figure 12:
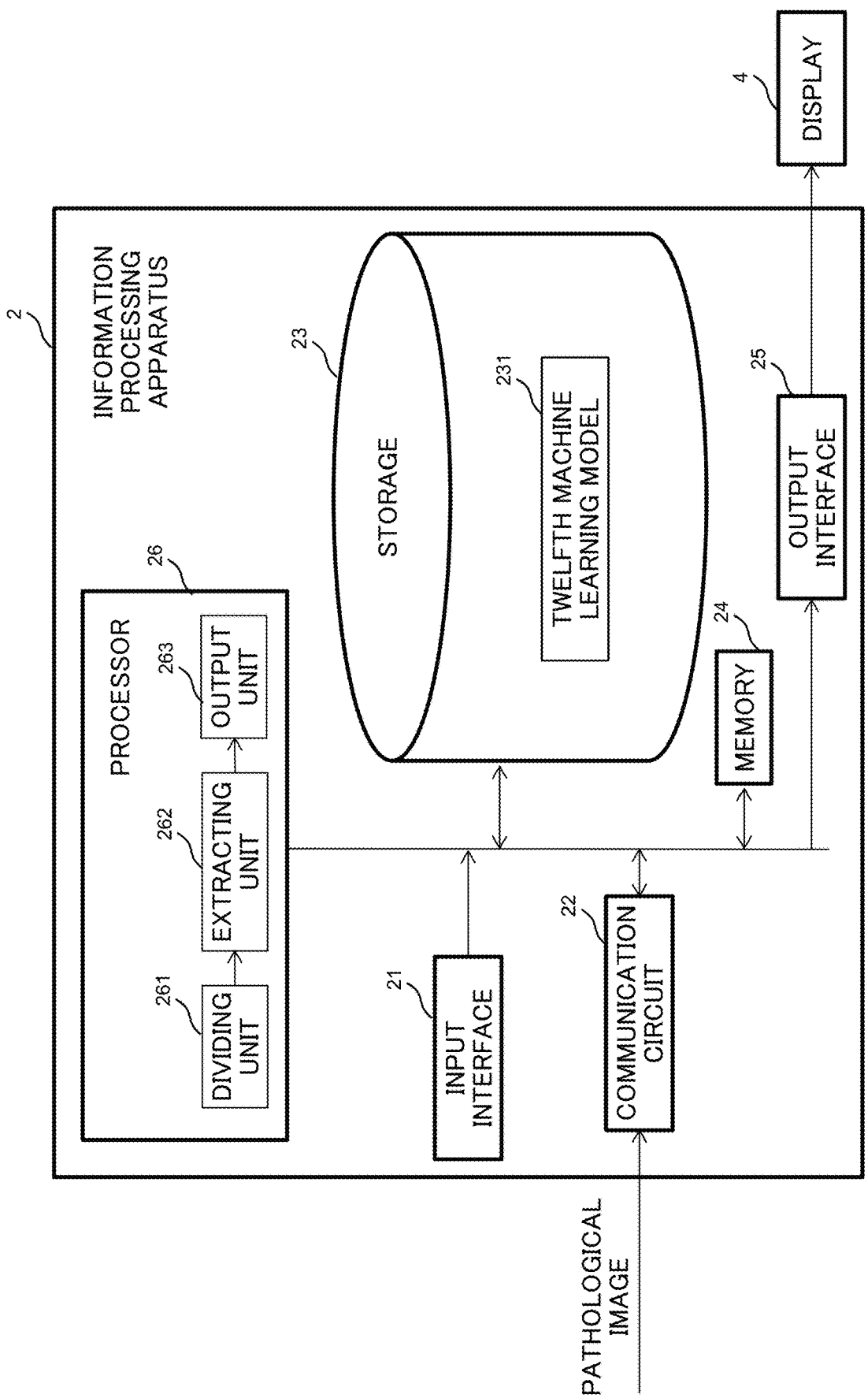
FIG. 12 is a schematic configuration diagram of an information processing apparatus according to the present embodiment.

FIG. 12 is a schematic configuration diagram of an information processing apparatus according to the present embodiment. As illustrated in FIG. 12, the information processing apparatus 2 includes an input interface 21, a communication circuit 22, a storage 23, a memory 24, an output interface 25, and a processor 26.

The input interface 21 receives an input from the administrator of the information processing apparatus 2 and outputs an input signal corresponding to the received input to the processor 26.

The communication circuit 22 is connected to the communication circuit network CN and communicates with the terminals 1-1 to 1-M or the administrator terminal 3 connected to the communication circuit network CN. Although this communication may be wired or wireless, description will be made as being wired.

The storage 23 stores programs and various pieces of data to be read and executed by the processor 26. The storage 25 stores, for example, a twelfth machine learning model 231.

The memory 24 temporarily holds data and programs. The memory 24 is a volatile memory, and is, for example, a random access memory (RAM).

The output interface 25 is an interface that connects to an external device and that outputs a signal to the external device. The output interface 25 is connected to, for example, the display 4, and can output a video signal to the display 4.

The processor 26 functions as a dividing unit 261, an extracting unit 262, and an output unit 263 by loading a program from the storage 23 into the memory 24 and executing a series of instructions included in the program.

As illustrated in FIG. 3, the dividing unit 261 divides the pathological image of the target cancerous tissue into a plurality of image regions (rectangular image regions in the example of FIG. 3).

The extracting unit 262 extracts an image area with a background occupying a set ratio or less from each of the image areas divided by the dividing unit 261.

The output unit 263 outputs information on whether a specific abnormality is present in the target object or information on whether a medicine corresponding to the specific abnormality is applicable to the target object by filtering the target image with a filter of a combination of features determined by the search method described in FIG. 2.

Here, as an example, the target object is cancerous tissue of the target patient, the image of the target object is a pathological image of the cancerous tissue of the target patient, and the specific abnormality is a specific genetic abnormality. In this premise, for example, the output unit 263 outputs information on whether a specific genetic abnormality is present in the cancerous tissue of the target patient or information on whether a medicine corresponding to the specific genetic abnormality is applicable to the target patient by filtering each image region having a background of less than or equal to a set ratio extracted from the image region obtained by dividing the pathological image of the cancerous tissue of the target patient with a filter of a combination of features determined by the search method illustrated in FIG. 10.

In the present embodiment, this filter is a filter using a trained machine learning model machine-learned using training data filtered by a filter of a combination of features determined by the search method illustrated in FIG. 10 for all training data. Here, as an example, the trained machine learning model is the twelfth machine learning model 231.

Figure 13:
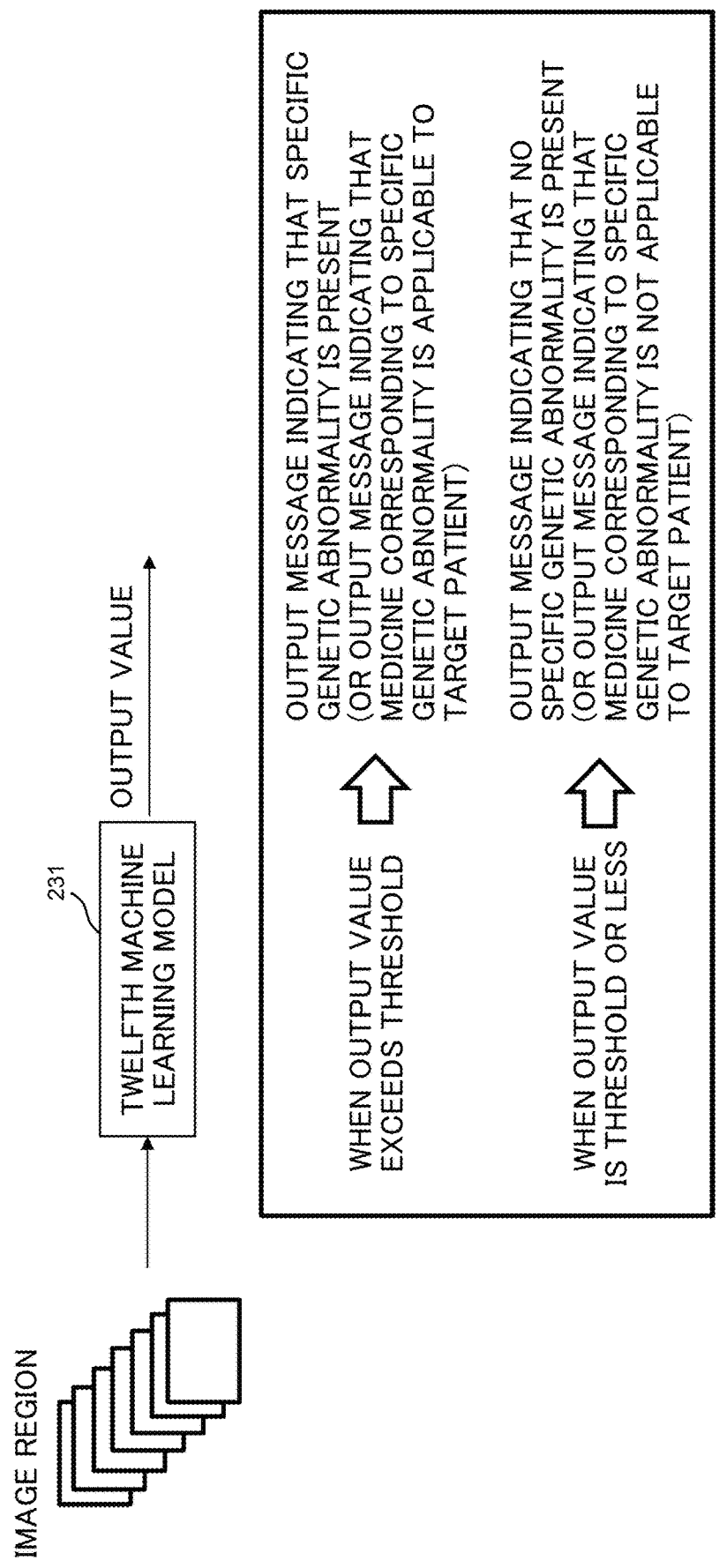
FIG. 13 is a schematic diagram that describes processing of an output unit according to the present embodiment.

FIG. 13 is a schematic diagram that describes processing of the output unit according to the present embodiment. FIG. 13 is a processing outline of the output unit of (when the feature is A+, C+, or D+, a specific genetic abnormality is present) in the case in which the machine learning model with the highest evaluation index is the twelfth machine learning model. As illustrated in FIG. 13, the output unit 263 inputs, to the twelfth machine learning model 231, each of image regions in which the background extracted from each of the image regions obtained by dividing the pathological image of the cancerous tissue of the target patient of which whether the specific genetic abnormality is present is the set ratio or less to acquire the output value. In the case in which the output value exceeds the threshold value, the output unit 263 outputs a message indicating that a specific genetic abnormality is present or that a medicine corresponding to the specific genetic abnormality is applicable to the target patient. On the other hand, in the case in which the output value is the threshold value or less, it is output that no specific genetic abnormality is present or that the medicine corresponding to the specific genetic abnormality is not applicable to the target patient.

As described above, the information processing system S according to the present embodiment includes an output unit that outputs information on whether the specific abnormality is present in the target object or information on whether a medicine corresponding to the specific abnormality is applicable to the target object by filtering an image of the target object with a filter of a combination of features determined by the search method in FIG. 2 or 10.

With this configuration, information on whether the specific abnormality is present in the target object or information on whether the medicine corresponding to the specific abnormality is applicable to the target object is output from the image of the target object, and thus it is possible to provide an index on whether the medicine corresponding to the specific abnormality can be prescribed to the target patient in a shorter period of time.

In the present embodiment, as an example, this filter is a filter using a trained machine learning model machine-learned using training data filtered by a filter of a combination of features determined by the search method described in FIG. 2 or 10 for all training data.

With this configuration, the trained machine learning model is used, and thus it is possible to improve prediction accuracy on whether the specific abnormality is present in the target object or whether the medicine corresponding to the specific abnormality is applicable to the target object.

In the present embodiment, the target object is cancerous tissue of a target patient, the image of the target object is a pathological image of the cancerous tissue of the target patient, and the specific abnormality is a specific genetic abnormality. The output unit 263 outputs information on whether the specific genetic abnormality is present in the cancerous tissue of the target patient or information on whether a medicine corresponding to the specific genetic abnormality is applicable to the target patient by filtering each of image regions obtained by dividing a pathological image of the cancerous tissue of the target patient with a filter of a combination of features determined by the search method illustrated in FIG. 2 or 10.

According to this configuration, information on whether the specific genetic abnormality is present in the cancerous tissue of the target patient or information on whether the medicine corresponding to the specific genetic abnormality is applicable to the target patient is output from the pathological image, and thus it is possible to provide an index on whether the medicine corresponding to the specific genetic abnormality can be prescribed to the target patient in a shorter period of time than DNA sequencing.

MODIFICATION

Figure 14:
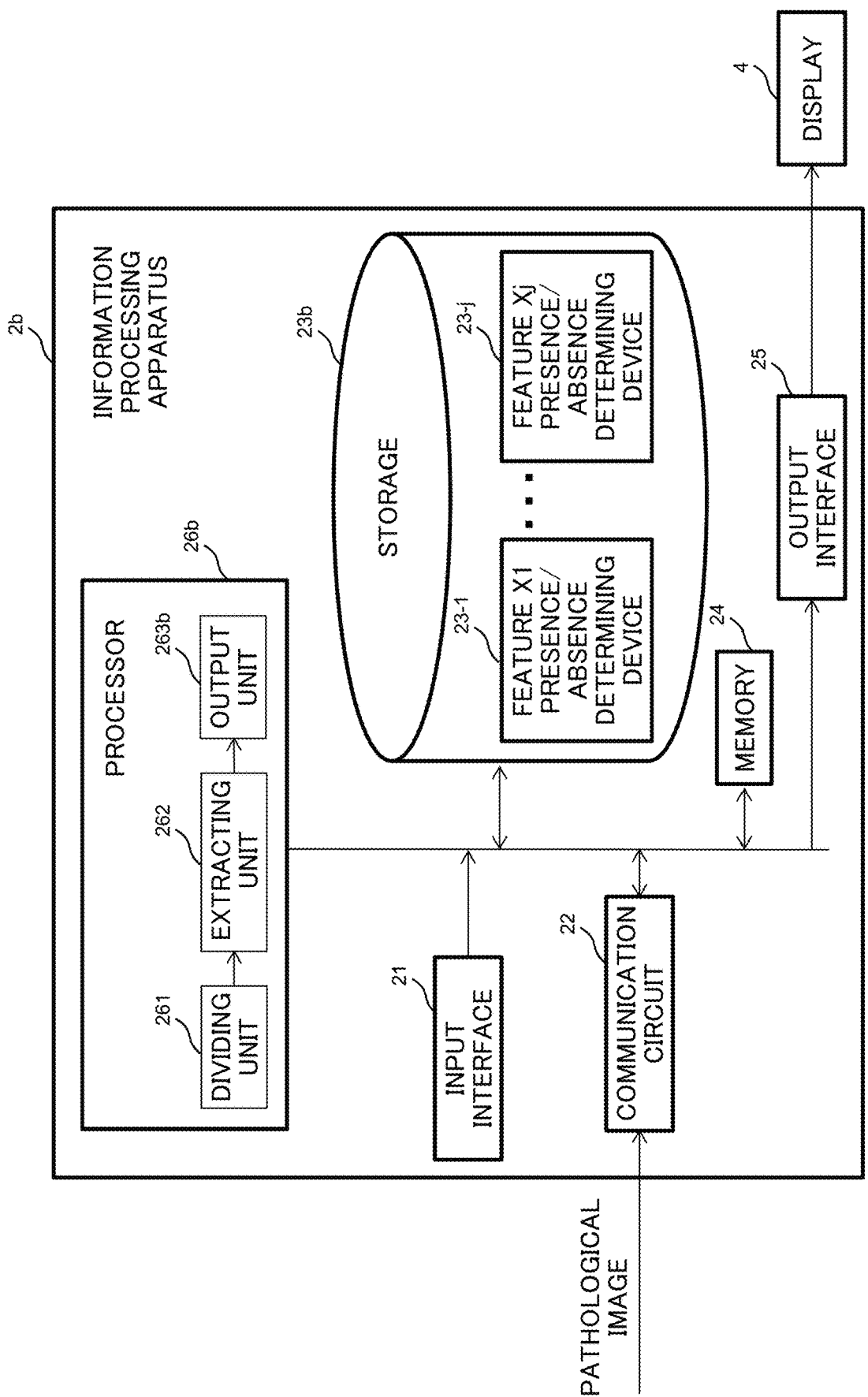
FIG. 14 is a schematic configuration diagram of an information processing apparatus according to a modification of the present embodiment.

Next, a modification of the information processing apparatus will be described with reference to FIGS. 14 and 15. FIG. 14 is a schematic configuration diagram of an information processing apparatus according to a modification of the present embodiment. The same components as those in FIG. 12 are designated with the same reference numerals, and the description will be omitted. Unlike FIG. 12, an information processing apparatus 2b according to the modification of the present embodiment in FIG. 14 stores a feature X1 presence/absence determining device, . . . , and a feature Xj presence/absence determining device (j is a natural number) in a storage 23b, and functions as an output unit 263b of a processor 26b. The output unit 263b applies a filter using the feature X1 presence/absence determining device, . . . , and the feature Xj presence/absence determining device (j is a natural number) described in the storage 23b to each of the image regions with backgrounds occupying the set ratio or less the backgrounds being extracted from the image regions obtained by dividing the pathological image of the cancerous tissue of the target patient.

FIG. 15 is a schematic diagram that describes processing of the output unit according to the modification of the present embodiment. Here, the processing outline of the output unit 263b is described in the case in which a specific genetic abnormality is present when feature A+, feature C+, and feature D+ are present.

The output unit 263b applies the filter 5, which is a combination of the feature A presence/absence determining device and the feature C presence/absence determining device, and the filter 8, which is a combination of the feature D presence/absence determining device, to each of the image regions in which the background extracted from the image region obtained by dividing the pathological image of the cancerous tissue of the target patient occupies the set ratio or less. In the case in which at least one image region is output after filtering, the output unit 263b outputs a message indicating that a specific genetic abnormality is present or that a medicine corresponding to the specific genetic abnormality is applicable to the target patient. On the other hand, in the case in which no image region is output after filtering, it is output that no specific genetic abnormality is present or that a medicine corresponding to the specific genetic abnormality is not applicable to the target patient.

According to this configuration, information on whether the specific genetic abnormality is present in the cancerous tissue of the target patient or information on whether the medicine corresponding to the specific genetic abnormality is applicable to the target patient is output from the pathological image, and thus it is possible to provide an index on whether the medicine corresponding to the specific genetic abnormality can be prescribed to the target patient in a shorter period of time than DNA sequencing.

It should be noted that at least a part of the information processing apparatus 2 described in the above-described embodiment may be configured using hardware or software. In the case in which the information processing apparatus 2 is configured using hardware, a program for realizing at least some functions of the information processing apparatus 2 may be stored in a recording medium such as a flexible disk or a CD-ROM, and may be read and executed by a computer. The recording medium is not limited to a removable recording medium such as a magnetic disk or an optical disk, and may be a fixed recording medium such as a hard disk device or a memory.

In addition, a program for realizing at least some functions of the information processing apparatus 2 may be distributed via a communication line (including wireless communication) such as the Internet. Further, the program may be distributed via a wired line or a wireless line such as the Internet or stored in a recording medium in an encrypted, modulated, or compressed state.

Furthermore, the information processing apparatus 2 may be caused to function using one or a plurality of information processing apparatuses. In the case of using a plurality of information processing apparatuses, one of the information processing apparatuses may be a computer, and the function may be realized as at least one unit of the information processing apparatus 2 by the computer executing a predetermined program.

In the invention of a method, all the processes (steps) may be realized by automatic control by a computer. In addition, the progress control between the processes may be performed by a human hand while causing a computer to perform each process. Furthermore, at least a part of all steps may be performed by a human hand.

As described above, the present invention is not limited to the above-described embodiment as it is, and can be embodied by modifying the components without deviating from the gist of the present invention in the implementation stage. In addition, various inventions can be formed by appropriately combining a plurality of constituent elements disclosed in the above embodiment. For example, some components may be deleted from all the components shown in the embodiments. Furthermore, constituent elements in different embodiments may be appropriately combined.

REFERENCE SIGNS LIST

1, 1-1 to 1-M Terminal
2, 2b Information processing apparatus
21 Input interface
22 Communication circuit
23 Storage
23-1 Feature X1 presence/absence determining device
23-j Feature Xj presence/absence determining device
231 Twelfth machine learning model
24 Memory
25 Output interface
26, 26b Processor
261 Dividing unit
262 Extracting unit
263, 263b Output unit
3 Administrator terminal
4 Display
CN Communication circuit network
S Information processing system

What is claimed is:

1. A computer-implemented search method of searching for a feature that affects an output result of a machine learning model, the computer-implemented search method comprising:
   a first step of applying, to all training data, at least one or more separate filters combining at least one or more feature presence/absence determining devices that determine presence or absence of a feature on a plurality of sets of correct answer data that is positive and correct answer data that is negative and information on whether the pieces of the data is positive;
   a second step of applying the pieces of training data generated in the first step to separate machine learning to separately execute machine learning; and
   a third step of outputting information that extracts a new feature using a verification result obtained by inputting verification data to separate machine learning after the machine learning.

2. The computer-implemented search method according to claim 1, further comprising:
   a fourth step of determining whether the training data occupies a setting ratio or less of all the training data on the pieces of training data generated in the first step;
   a fifth step of excluding, as a result of the determination in the fourth step, when the training data occupies a setting ratio or less of all the training data, a set of feature presence/absence determining devices corresponding to a combination of features including a set of features corresponding to the training data;
   a sixth step of applying, to at least one or more pieces of all the training data, separate filters configured of at least one or more sets except the excluded set of feature presence/absence determining devices in the at least one feature presence/absence determining device and a feature presence/absence determining device that determines whether the presence or absence of the newly extracted feature;
   a seventh step of applying the pieces of training data generated in the sixth step to separate machine learning to separately execute machine learning; and
   an eighth step of outputting, after the machine learning in the seventh step, information that extracts a new feature using a verification result obtained by inputting verification data to the separate machine learning.

3. The computer-implemented search method according to claim 2, further comprising:
   a ninth step in which when a new feature is extracted in the eighth step, the fourth step is further executed on the pieces of training data generated in the sixth step, the fifth step, the sixth step, the seventh step, and the eighth step are repeated correspondingly,
   wherein when no new feature is extracted after the information that extracts a new feature is output in the eighth step, a machine learning model having performance that satisfies a setting requirement is extracted from machine learning models corresponding to combinations of features so far, and a combination of features corresponding to the extracted machine learning model is output.

4. The computer-implemented search method according to claim 1, wherein:
   the search method is a search method of searching for a feature that is a feature of an image of a target object and that affects an output result of whether a specific abnormality is present in the target object,
   in the first step, at least one or more separate filters combining at least one or more feature presence/absence determining devices that determine presence or absence of a feature are applied, to all training data, on a plurality of sets of an image of a target object having a specific abnormality and an image of a target object having no specific abnormality and information whether the target objects from which the images are obtained have a specific abnormality, and the feature that affects the output result of the machine learning model is a feature that determines whether a specific abnormality is present in the target object.

5. The computer-implemented search method according to claim 4, wherein:
the target object is cancerous tissue of a patient,
the image of the target object is a pathological image of cancerous tissue of the patient,
the specific abnormality is a specific genetic abnormality, and
in the first step, at least one or more separate filters combining at least one or more feature presence/absence determining devices that determine presence or absence of a feature are applied, to all training data, on a plurality of sets of an image region of a pathological image of cancerous tissue with a specific genetic abnormality and an image region of a pathological image of cancerous tissue with no specific genetic abnormality or normal tissue and information on whether a specific genetic abnormality is present in a patient's tissue from which each image region has been obtained.

6. A computer-implemented method comprising: an output step of outputting information on whether the specific abnormality is present in a target object or information on whether a medicine corresponding to the specific abnormality is applicable to the target object by filtering a target image with a filter of a combination of features determined by the search method according to claim 3.

7. The computer-implemented method according to claim 6, wherein the filter is a filter using a trained machine learning model machine-learned using training data filtered by a filter of a combination of features determined by the search method.

8. The computer-implemented method according to claim 6, wherein:
the target object is cancerous tissue of a target patient,
the image of the target object is a pathological image of cancerous tissue of a target patient,
the specific abnormality is a specific genetic abnormality, and
the method comprises the output step that outputs information on whether the specific genetic abnormality is present in the cancerous tissue of the target patient or information on whether a medicine corresponding to the specific genetic abnormality is applicable to the target patient by filtering each of image regions obtained by dividing a pathological image of the cancerous tissue of the target patient using a filter with a combination of features determined by the search method.

9. A computer-implemented search system of searching for a feature that affects an output result of a machine learning model, the computer-implemented search system comprising:
at least one memory storing instructions; and
at least one processor configured to execute the instructions to perform:
a first step of applying, to all training data, at least one or more separate filters combining at least one or more feature presence/absence determining devices that determine presence or absence of a feature on a plurality of sets of correct answer data that is positive and correct answer data that is negative and information on whether the pieces of the data is positive;
a second step of applying the pieces of training data generated in the first step to separate machine learning to separately execute machine learning; and
a third step of outputting information that extracts a new feature using a verification result obtained by inputting verification data to separate machine learning after the machine learning.

* * * * *